US005195961A

United States Patent [19]
Takahashi et al.

[11] Patent Number: 5,195,961
[45] Date of Patent: Mar. 23, 1993

[54] ASPIRATOR

[75] Inventors: Susumu Takahashi; Yoshihiro Takahashi; Mineki Hayafuji, all of Tokyo, Japan

[73] Assignee: Kabushiki Kaisha Topcon, Japan

[21] Appl. No.: 427,132

[22] PCT Filed: Apr. 19, 1989

[86] PCT No.: PCT/JP89/00417

§ 371 Date: Mar. 18, 1991

§ 102(e) Date: Mar. 18, 1991

[30] Foreign Application Priority Data

Apr. 20, 1988 [JP] Japan .................................. 63-95738
May 12, 1988 [JP] Japan ................................ 63-113636
Jul. 25, 1988 [JP] Japan ................................ 63-183563

[51] Int. Cl.$^5$ .............................................. A61M 1/00
[52] U.S. Cl. .................................... 604/35; 604/236
[58] Field of Search ........................ 604/236, 30, 35

[56] References Cited

U.S. PATENT DOCUMENTS

| | | | |
|---|---|---|---|
| 4,168,707 | 9/1979 | Douvas et al. | 604/35 |
| 4,274,411 | 6/1981 | Dotson, Jr. | 604/30 |
| 4,369,785 | 1/1983 | Rehkopf et al. | 604/35 |
| 4,493,695 | 1/1985 | Cook | 604/30 |
| 4,604,089 | 8/1986 | Santangelo et al. | 604/30 |
| 4,650,462 | 3/1987 | DeSatnick et al. | 604/30 |
| 4,670,006 | 6/1987 | Sinnett et al. | 604/35 |
| 4,935,005 | 6/1990 | Haines | 604/35 |

Primary Examiner—Paul J. Hirsch
Attorney, Agent, or Firm—Lorusso & Loud

[57] ABSTRACT

The present invention relates to an aspirator for aspirating materials to be removed within the eyeball. The materials are an infusion or the viterous body.

A conventional aspirator permits no easy provision of an arbitrary pressure. In accordance with the present invention, a pressure adjusting unit (90) is disposed to connect an accommodating unit (100) to the air through an opening (96) of a variable size.

For such a conventional aspirator, it is required that aspiration should be interrupted as a bottle is full with the removed materials. For the present invention, there are provided a first accommodating unit (2100), a second accommodating unit (2101) and a third accommodating unit (2102). The third accommodating unit (2102) has a capacity larger than each of the first and second accommodating units (2100, 2101). These accommodating units are connected.

Furthermore, such a conventional aspirator may not ensure a safety in surgery. In accordance with the present invention, a flexible passage portion (3020) is disposed in the main body (3005) of the aspirator in such a manner that the passage portion (3020) is opened or closed by operation of a materials-passage opening/closing unit (3003).

15 Claims, 16 Drawing Sheets

ASPIRATOR

BACKGROUND OF THE INVENTION

1. Field of the Invention

The present invention relates to an aspirator to be used for ophthalmic surgery of the vitreous body and a cataract.

2. The Related Prior Art (1) An aspirator for ophthalmic surgery removes a translucent portion of the vitreous body in the eyeball by suction. The aspirator may include, for example, one bottle. The bottle is provided with two passages. One of the passages is connected to a vacuum pump and the other communicates with the open air. Control of opening or closing the two passages by the vacuum pump can adjust the pressure in the bottle and the translucent portion of the vitreous body is sucked into the bottle by means of vacuum in the bottle.

It is to be noted, however, that control apparatus becomes complicated when control over the opening o closing of the two passages is be required.

(2) An aspirator (M) for surgery is provided with two bottles, larger and smaller, and the two bottles are connected to each other through a pipe. The pipe is further provided at its intermediate portion with a branch pipe which, in turn, is connected to a surgical apparatus and which is further provided with a valve for controlling the flow rate of materials to be aspirated and sucked through the pipe.

Another aspirator (N) for ophthalmic surgery is provided with one bottle which, in turn, is fitted with a conduit for supplying vacuum and with a conduit for communicating the pressure in the bottle with ambient air. A valve is mounted on each of the conduits and the pressure in the bottle is adjusted to a predetermined pressure by controlling each of the valves.

It is to be noted, however, that the former aspirator (M) must interrupt aspiration of materials to be aspirated and sucked during the period of time when the aspirated materials stored in the smaller bottle are to be transferred to the larger bottle. This leads to frequent interruptions in the surgery.

For the latter aspirator (N), only one bottle is used so that the time required to each the predetermined pressure necessary for aspiration varies with the quantity of the sucked materials stored in the bottle. For instance, when a bottle is large in volume and empty, the time required for aspiration becomes too long.

(3) Furthermore, conveyance of the sucked materials through a flexible passage portion in an aspirating cassette, when the aspirator having a materials-passage opening/closing unit of this type is suspended, by pressing a portion of the materials-passage opening/closing unit in the aspirator onto the flexible passage portion in response to a signal. Conveyance of the aspirated materials through the passage portions is resumed by returning the portion of the materials-passage opening/closing unit to its original by discontinuing the pressing onto the passage portion.

It is, however, to be noted that the above-mentioned aspirator is such that the force for squeezing the passage portion by means of the portion of the materials-passage opening/closing unit is also applied to the aspirating cassette when conveying the aspirated materials through the flexible passage portion, in other words, upon or during pressing the portion of the materials-passage opening/closing unit onto the aspirating cassette.

In this case, the aspirating cassette may be inclined by the force applied, thus breaking the connection of an accommodating unit in the aspirating cassette with a vacuum controlling unit in the main body of the aspirator itself or causing the aspirating cassette to come off from the main body of the aspirator. This may incur the risk of interfering with the surgery and endangers the safety of the surgery.

SUMMARY OF THE INVENTION (1) The present invention has as an object to provide an aspirator in which pressure can be readily adjusted by a simple procedure in order to produce a predetermined pressure.

More specifically, the present invention may be constituted, for example, by the following structure as shown in FIGS. 2 and 3.

An aspirating unit 30 aspirates materials 34 to be removed.

An accommodating unit 100 collects materials 34 aspirated by the aspirating unit 30.

A pressure reducing unit 130 reduces the pressure of the accommodating unit 100 to a constant vacuum pressure.

A pressure detecting unit 111 detects the pressure in the accommodating unit 100.

A pressure adjusting unit 90 vents the accommodating unit 100 to the ambient air through an opening 96 of a variable size.

A pressure controlling unit 180 controls the pressure in the accommodating unit 100 by adjusting the size of the opening 96 of the pressure adjusting unit 90 on the basis of the pressure detected by the pressure detecting unit 111.

The pressure within the accommodating unit 100 is adjusted by communicating the inside of the accommodating unit 100 with the ambient air by changing the size of the opening 96. This allows a free adjustment of the pressure within the accommodating unit 100.

Another example will be described with reference to FIGS. 10 and 11.

The aspirating unit 30 aspirates materials 34 to be removed.

A first accommodating unit 600 receives the materials 34 aspirated by the aspirating unit 30.

A second accommodating unit 601 is connected to the first accommodating unit 600 and accommodates the aspirated materials 34 which have been transferred from the first accommodating unit 600.

A pressure reducing unit 630 is connected to the first accommodating unit 600 and the second accommodating unit 601 to reduce the pressure thereof at a constant vacuum pressure.

A pressure detecting unit 611 detects the pressure of the first accommodating unit 600.

A pressure adjusting unit 590 communicates the first accommodating unit 600 with the ambient air through an opening 596 with a variable size.

A pressure controlling unit 680 controls the pressure within the first accommodating unit 600 at a constant pressure by adjusting the size of the opening 596 of the pressure adjusting unit 590 on the basis of the pressure detected by the pressure detecting unit 611.

A further example will be described with reference to FIGS. 12 and 13.

An accommodating unit 30 aspirates materials 34 to be removed by suction.

A first accommodating unit 1100 accommodates the materials 34 aspirated by the aspirating unit 30.

A second accommodating unit 1102 to connected to the first accommodating unit 1100 and accommodates the materials 34 which have been transferred from the first accommodating unit 1100.

A pressure reducing unit 1130 reduces the pressure within the first accommodating unit 1100 to maintain a constant vacuum pressure.

A pressure detecting unit 1111 detects a pressure within the first accommodating unit 1100.

A pressure adjusting unit 1090 connects the first accommodating unit 1100 to the ambient air through an opening 1096 with a variable size.

A pressure controlling unit 1180 adjusts the pressure of the first accommodating unit 1100 to a given pressure by adjusting the size of the opening 1096 of the pressure adjusting unit 1090 on the basis of the pressure detected by the pressure detecting unit 1111.

(2) The present invention also has an object to provide an aspirator capable of bringing pressure to a predetermined level required for aspiration within a constantly short period of time without interruption of aspiration of materials to be removed.

The present invention is described with reference to FIG. 15 as comprising an aspirating unit 2001 which aspirates materials 2034 to be removed by means of vacuum.

A first accommodating unit 2100 accommodates the materials 2034 to be removed while a second accommodating unit 2101 accommodates the materials 2034 in the same manner as the first accommodating unit 2100.

A third accommodating unit 2102 has a capacity larger than each of the first and second accommodating units 2100 and 2101, respectively, and accommodates the materials 2034 to be removed.

An aspirating mouth portion 2030 aspirates and sucks the materials 2034 to be removed.

A first passage 2008 leads the materials 2034 from the aspirating mouth portion 2030 to the first accommodating unit 2100.

A first pressure adjusting unit 2070 adjusts the pressure within the first accommodating unit 2100.

A second pressure adjusting unit 2340 adjusts the pressure within the second accommodating unit 2101 (through an air reservoir 2300, for example).

A second passage 2088 is disposed separately from the first passage 2008 and leads the materials 2034 within the first accommodating unit 2100 to the second accommodating unit 2101.

A first valve 2210 is disposed on the second passage 2088 and opens or closes the passage of materials 2034 from the second accommodating unit 2101 to a third accommodating unit 2101.

A third passage 2188 is disposed separately from the second passage 2088 and leads the materials 2034 within the second accommodating unit 2101 to the third accommodating unit 2102. A second valve 2220 is disposed in the third passage 2188 and opens or closes the passage of the materials 2034 through the third passage 2188.

The first pressure adjusting unit 2070 reduces the pressure within the first accommodating unit 2100, thus leading the materials 2034 from the aspirating mouth portion 2030 through the first passage 2008 to the first accommodating unit 2100. The second pressure adjusting unit 2340 adjusts the pressure within the second accommodating unit 2101 (through the air reservoir 2300) to become equal to or lower than that within the first accommodating unit 2100, thus controlling the first valve 2210 and leading the materials 2034 to the second accommodating unit 2101 through the second passage 2088.

Furthermore, the pressure within the second accommodating unit 2101 is made equal to or higher than that within the third accommodating unit 2102 by means of the second pressure adjusting unit 2340 (through the air reservoir 2300) by closing the first valve 2210, thus controlling the second valve 2220 and leading the materials 2034 to the third accommodating unit 2102 through the third passage 2188.

A preferred embodiment will be described.

The first accommodating unit 2100 is provided with a first accommodating level detecting unit 2112 for detecting a predetermined level A for the materials 2034 accommodating unit 2100 and with a second accommodation level detecting unit 2113 for detecting a predetermined level B of the removed materials 2034.

When the first accommodation level detecting unit 2112 has detected the state in which the materials are held in a large amount in the first accommodating unit, the first valve 2210 is opened thus allowing the materials within the first accommodating unit 2100 to be led to the second accommodating unit 2101 through the second passage 2088. When the second accommodation level detecting unit 2113 has detected the state in which the materials are reduced to level B, the first valve 2210 is closed.

The first pressure adjusting unit 2070 contains a first pressure detector 2111 capable of detecting the pressure within the first accommodating unit 2100. If the first pressure detector 2111 detects that the pressure within the first accommodating unit 2100 is elevated to a level higher than a predetermined pressure, the pressure to be supplied by the first pressure adjusting unit 2070 is reduced to thereby reduce the pressure within the first accommodating unit 2100. If it detects a pressure within the first accommodating unit 2100 lower than the predetermined pressure, the pressure to be supplied by the first pressure adjusting unit 2070 is elevated and then supplied to the first accommodating unit 2100. This permits the pressure within the first accommodating unit 2100 to be kept at a substantially constant level.

The second pressure adjusting unit 2340 contains a second pressure detector 2315 for detecting the pressure within the second accommodating unit 2101. When the second pressure detector 2315 has detected a pressure within the second accommodating unit 2101 higher than a predetermined pressure, on the one hand, the pressure to be supplied by the second pressure adjusting unit 2340 is reduced to thereby reduce the pressure within the second accommodating unit 2101. When it has detected a pressure level within the second accommodating unit 2101 lower than the predetermined pressure, pressure to be fed by the second pressure adjusting unit 2340 is elevated and then supplied to the second accommodating unit 2101. This enables the pressure within the second accommodating unit 2101 to be kept at a substantially constant level.

The pressures only within the first and second accommodating units 2100 and 2101 with smaller volumes, respectively, are maintained at the predetermined pressures.

This construction permits aspiration of the materials 2034 to be continued without interruption of surgery during a transferral of the materials 2034 from the first accommodating unit 2100 to the second accommodating unit 2101 as well as from the second accommodating unit to the third accommodating unit 2102.

(3) Furthermore, the present invention has the object to provide an aspirator in which the aspirating container unit is not inclined or detached from the main body of the aspirator due to a force to the aspirating container unit by means of operation of the materials-passage opening/closing unit.

The present invention is constituted by the following construction.

The present invention will be described with reference to Example 1 in FIG. 19.

An aspirator 3001 is a device that aspirates materials 3021 to be removed from the eyeball 3030 by means of vacuum and holds it in an accommodating unit 3022. The aspirator 3001 includes at least a vacuum controlling unit 3002, a main housing 3005 for the aspirator, an aspirating container unit (an aspirating cassette 3004) mounted detachably on the main housing 3005, and a materials-passage opening/closing unit 3003.

The aspirating cassette 3004 includes an aspirating mouth portion 3032 for aspirating and sucking materials 3021 to be removed, one or plural accommodating units (one bottle 3022) for accommodating the aspirated materials 3021, and a flexible passage portion (a flexible tube 3020) interconnected between the aspirating mouth portion 3032 and the bottle 3022 for transferring the materials 3021.

When the materials-passage opening/closing unit 3003 is released transferal of the materials 3021 in the flexible tube 3020 can be achieved without any force applied to the aspirating cassette 3004.

In the embodiment of FIG. 21, flexible tubes 3221 and 3222 are connected to bottles 3200, 3201, and 3202. Aspirating mouth portion 3223 and the bottle 3200 are connected by the flexible tube 3220.

As shown in FIG. 19, no force is applied to the aspirating cassette 3004 upon opening or closing the flexible tube 3020 by means of the materials-passage opening/closing unit 3003, thereby incurring n risk of the aspirating cassette being disconnected.

DESCRIPTION OF THE PREFERRED EMBODIMENTS

Example 1

Figure 1:
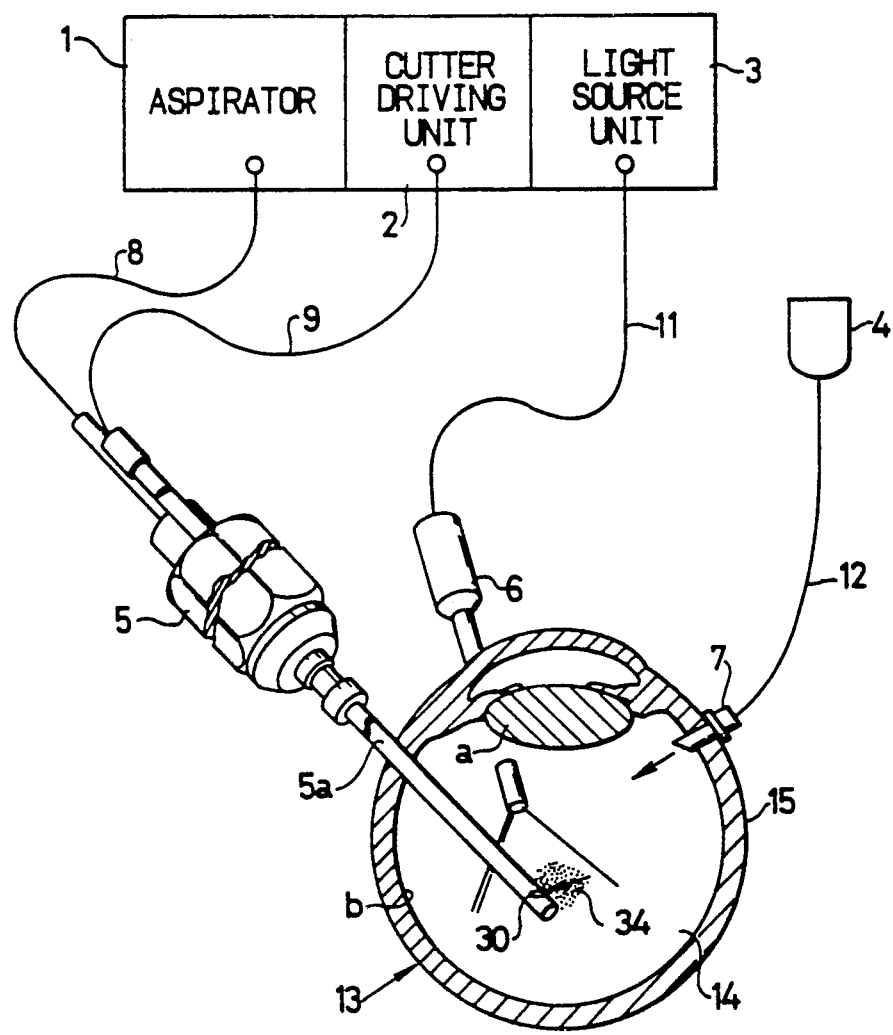
FIG. 1 is a representation showing the aspirator and other units in accordance with the present invention.

FIG. 1 shows a preferred embodiment of the aspirator according to the present invention. The aspirator 1 according to the present invention is mounted in a surgery apparatus for the vitreous body as one example.

In the surgery of the vitreous body, an unclear portion of the vitreous body 14 in a gel form (referred to herein as "removed material 34" and related terms) between the lens a and the retina b is removed by suction and replaced by a clear liquid. This enables light to reach the retina b through the lens a, thus improving sight.

Referring to FIG. 1, there are shown an aspirator 1, a cutter driving unit 2, a light source unit 3, an infusion bottle 4, a cutter 5 with a suction mechanism, a light guide 6, and an infusion plug 7.

The cutter 5 contains an insert portion 5a for insertion through the sclera 15 of the eyeball 13. At a tip portion of the insert portion 5a is provided an aspirating mouth portion 30. The cutter 5 is designed so as to cut the materials 34 which enter aspirating mouth portion 30 and the cut materials 34 are sucked into the aspirator 1 through the inside of the insert portion 5a and a first passage 8.

To the cutter driving unit 2 is connected a tube 9 for compressed air. Through the tube 9 is fed compressed air to the cutter 5 and the compressed air operates the cutter 5 to cut the materials 34. The light source unit 3 emits light to the light guide 6 through an optical fiber 11. A tip portion of the light guide 6 is inserted into the eyeball 13 and the light guide 6 can apply light around the aspirating mouth portion 30.

The infusion bottle 4 accommodates an infusion. The infusion is supplied to the inside of the eyeball 13 through an infusion tube 12 and the infusion plug 7. The infusion fills in the eyeball 13 in order to replace the removed materials 3 which have been cut and removed by suction, thereby recovering sight.

Aspirator 1

The aspirator 1 will be described more in detail with reference to FIGS. 2 and 3.

Figure 2:
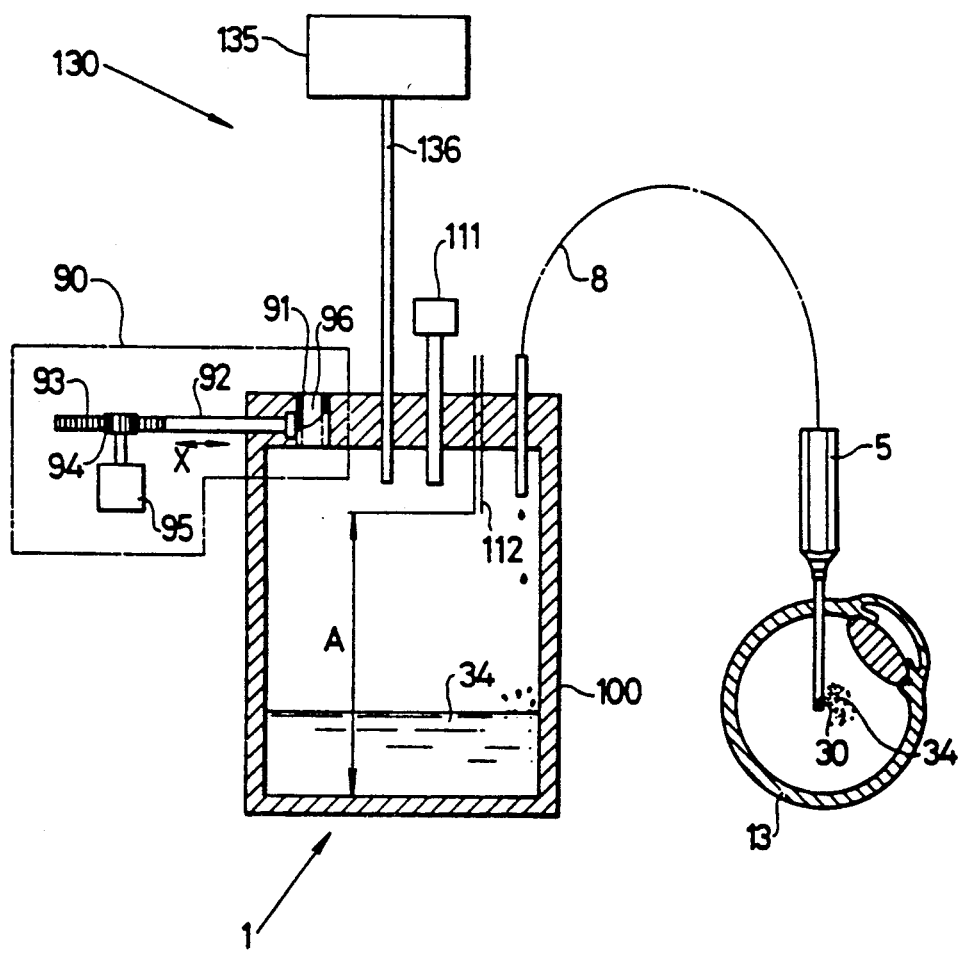
FIG. 2 is a view showing the aspirator of FIG. 1 according to the present invention.

As shown in FIG. 2, the aspirator 1 is a device to aspirate the removed materials 34 within the eyeball 13 by means of a negative pressure.

Accommodating Unit 100

The aspirator 1 contains an accommodating unit 100 in a bottle form. The accommodating unit 100 holds the removed materials 34.

The aspirating mouth portion 30 of the cutter 5 communicates with the first passage 8 and the first passage 8 extends so as to pass through the top lid of the first accommodating unit 100 to reach the inside thereof.

The first accommodating unit 100 is provided with an accommodation state detector 112 such as a liquid level detector. The accommodation state detector 112 detects the liquid level of the removed materials 34 as it comes to a position indicated by "A".

Pressure Reducing Unit 130

The pressure reducing unit 130 maintains the inside of the accommodating unit 100 always at a constant vacuum pressure. The pressure reducing unit 130 contains a vacuum pump 135 and a passage 136. The vacuum pump 135 communicates with the accommodating unit 100 through the passage 136.

Pressure Detecting Unit 111

The pressure detecting unit 111 is a pressure sensor. The pressure detecting unit 111 detects the inner pressure of the accommodating unit 100.

Pressure Adjusting Unit 90

The pressure adjusting unit 90 contains a flexible tube body 91, a pressing member 92, a rack 93, a pinion 94 and a motor 95.

The tube body 91 is composed, of an elastically transformable material such as rubber. The tube body 91 is mounted on the upper portion of the accommodating unit 100. The tube body 91 is provided with an opening 96 for air intake. The pinion 94 is mounted on an output shaft of the motor 95. The pinion 94 is in mesh with the rack 93. To the rack 93 is fixed the pressing member 92. Driving the motor 95 moves the pressing member 92 in the direction as indicated by the arrow X, varying the size of the opening 96 of the tube body 91.

Figure 3:
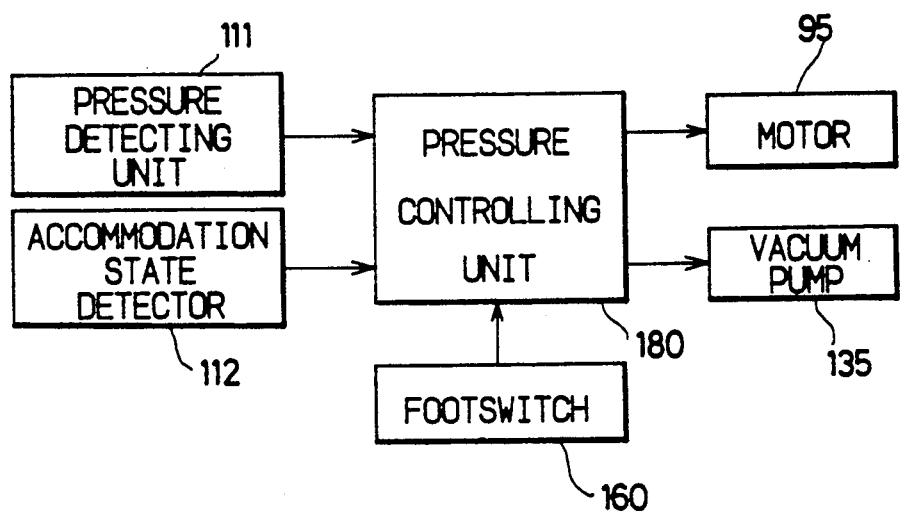
FIG. 3 is a diagram showing a control system for the first embodiment of FIG. 2.

As shown in FIG. 3, a pressure controlling unit 180 receives a signal from the pressure detecting unit 111, a signal from the accommodation state detector 112, and a signal from a foot switch 160. The pressure controlling unit 180 adjusts the size of the opening 96 by rotating the motor 95 on the basis of the signal from the pressure detecting unit 111. This adjusts the pressure within the accommodating unit 100 to a set pressure. The pressure controlling unit 180 is connected to the vacuum pump 135.

OPERATION

The operation will be described with reference to FIGS. 2 and 3.

As the foot switch 160 turns on, the vacuum pump 135 starts operating and the pressure within the inside of the accommodating unit 100 becomes negative. The materials 34 to be removed are led to the accommodating unit 100 through the aspirating mouth portion 30 and the passage 8.

The pressure detecting unit 111 constantly detects the pressure within the accommodating unit 100 and keeps transmitting signals to the pressure controlling unit 180.

If the pressure within the pressure controlling unit 180 is different from the set pressure, the accommodating unit 100 provides the motor 95 with a control signal in order to correct the pressure within the unit 180. Then the motor 95 starts moving the pressing member 92 on the basis of the signal and changes the size of the opening 96 of the tube body 91, thereby changing the amount of air entering the accommodating unit 100.

This permits the pressure within the accommodating unit 100 to be kept always at the set pressure.

During suction of the materials 34 to be removed, the accommodation state detector 112 determines that the amount of the materials 34 held in the accommodating unit 100 has reached a set volume. On the basis of a signal from the detector, the pressure controlling unit 180 gives an alarm or stops operation of the vacuum pump 135 in order to prevent an overflow of the materials 34 from the accommodating unit 100.

As a variant of Example 1, the tube body 91 may be located on a side portion or a bottom portion of the accommodating unit 100, instead of the top portion thereof. For the pressure adjusting unit 90, a crank mechanism or the like may be employed although the rack 93 and pinion 94 are employed therefor in this embodiment.

Example 2

Figure 4:
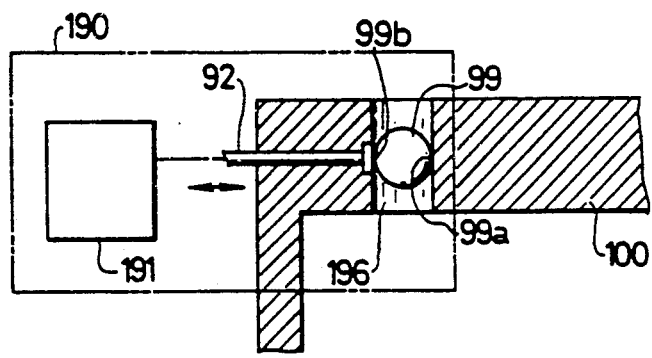
FIGS. 4 to 9 are views showing Examples 2 to 6, respectively.
Figure 5:
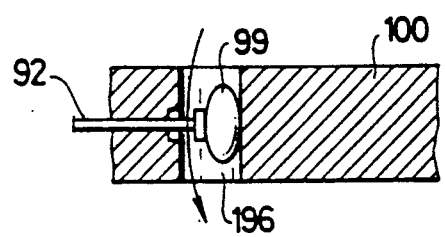

As shown in FIGS. 4 and 5, the pressure adjusting unit 190 is designed so as to press the pressing member 92 onto a side surface 99b of a member 99 having a spherical or cylindrical form.

Referring now to FIG. 4, the member 99 is disposed to close the opening 196 of the accommodating unit 100. An opposite side 99a of the member 99 is securedly fixed to the accommodating unit 100.

Referring then to FIG. 5, the member 99 is forcibly pressed by means of the pressing member 92. This allows the air to enter the accommodating unit 100 through the opening 196.

The member 99 may be conveniently chosen arbitrarily from an elastic material such as a water bag, air bag, a rubber and the like.

Example 3

Figure 6:
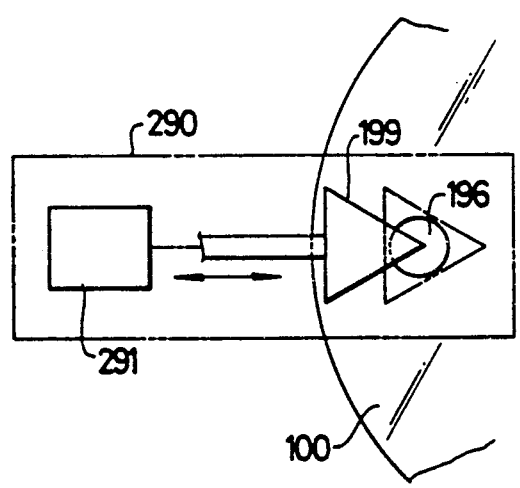

FIG. 6 is a view of the accommodating unit 100 when viewed from the top. The member 199 is displaced so as to change the sectional area of the opening 196. The member 199 of FIG. 6 may be of a triangular, circular or square form.

Example 4

Figure 7:
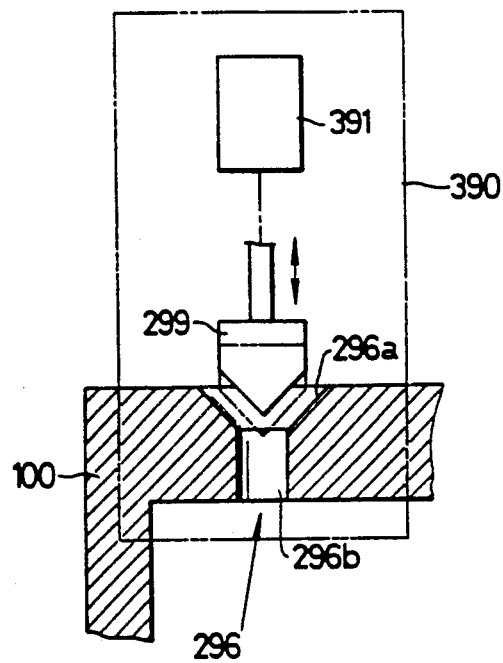

As shown in FIG. 7, the accommodating unit 100 is provided with an opening 296. The opening 296 comprises a tapered portion 296a and a small-diameter portion 296b. A member 299 is shaped in a form so as to mate with the tapered portion 296a. By adjusting the degree to which the member 299 is brought into contact with or disengaged from the tapered portion 296a, the amount of the air to be passed through the opening 296 can be changed.

It is to be noted, however, that the forms of the opening 296 and the member 299 are not restricted to the example as shown in FIG. 7.

Example 5

Figure 8:
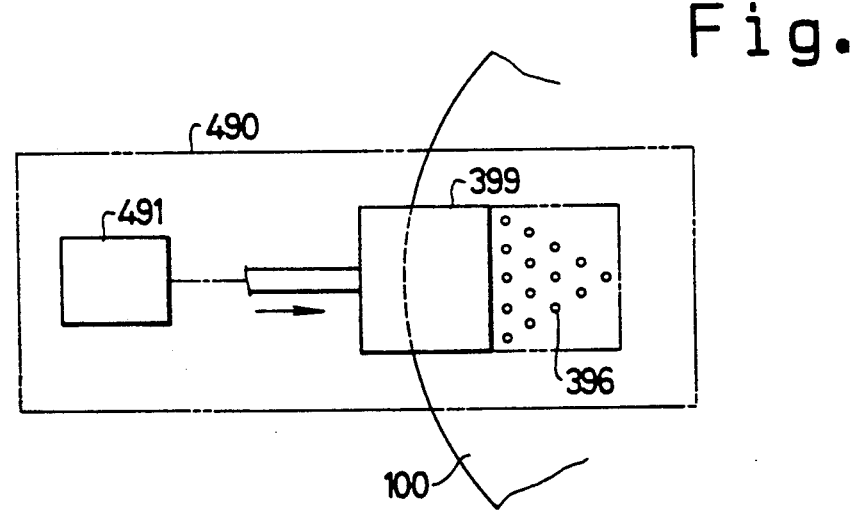

FIG. 8 is a view of the accommodating unit 100 when looked at from the top. The accommodating unit 100 is provided with a large number of small openings 396. These openings 396 are disposed in a triangular area. The member 399 is a plate which closes the openings 396. It is noted, however, that a disposition of the opening 396 is not restricted to such a triangular area.

Example 6

Figure 9:
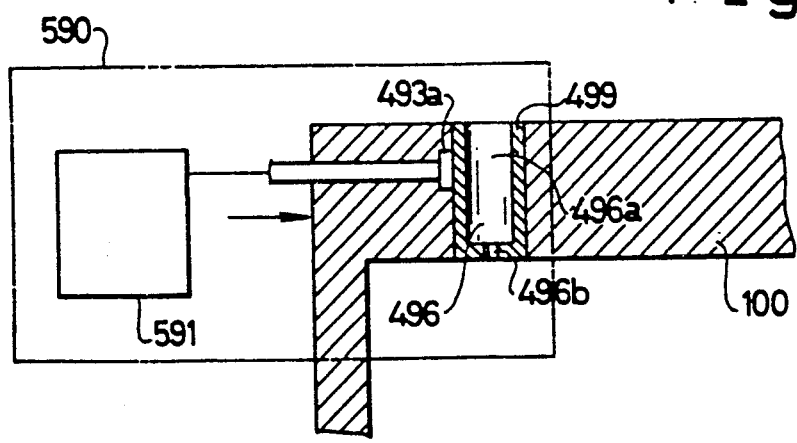

Referring to FIG. 9, opening 496 of a member 499 is shown to comprise a large-diameter portion 496a and a small-diameter portion 496b. More specifically, the large-diameter portion 496a is located on outside while the small-diameter portion 496b is located on the inside of the accommodating unit 100. This member 499 may be disposed so as to be pressed by means of a pressing member 493a. It is also possible that the small-diameter portion is located on the side of the air while the large-diameter portion is located o the side of the accommodating unit in such a manner that the large-diameter portion is pressed by means of the pressing member.

The driving unit 191 of the pressure adjusting unit 190 of FIG. 4, driving unit 291 of the pressure adjusting unit 290 of FIG. 6, driving unit 391 of a pressure adjusting unit 390 of FIG. 7, driving unit 491 of a pressure adjusting unit 490 of FIG. 8, or driving unit 591 of a pressure adjusting unit 590 of FIG. 9 may be used as the mechanism shown in FIG. 2 or a mechanism similar to that as shown therein.

As a further embodiment, for instance, a tube may be disposed in such a manner that it projects from the accommodating unit and either of the pressure adjusting units as shown in FIGS. 4 to 9 may be mounted thereto.

The tube may be curved to change the width of its air passage by bending or by other means.

As a valve, any of the pressure adjusting units of FIGS. 4 to 9 may be mounted on the passage 136 of FIG. 2.

Example 7

A description will be made with reference to FIG. 10.

An aspirator 501 is a device such that materials 34 to be removed in the eyeball 13 are aspirated by negative pressures.

Accommodating Units 600 & 601

The aspirator 501 is provided with first and second accommodating units 600 and 601, respectively, each in a bottle form. The accommodating units 600 and 601 hold the removed materials 34. The first and second accommodating units 600 and 601 have substantially the same capacities.

The aspirating mouth portion 30 of the cutter 5 is communicated with a first passage 508 and the first passage 508 is led through a top lid of a first accommodating unit 600 to the inside thereof. The first passage 508 is mounted with a first valve 509.

A second passage 588 is led from the bottom of the first accommodating unit 600 to the inside of the second accommodating unit 601. At an intermediate portion of the second passage 588 is mounted a second valve 710. A third passage 788 is led from the top lid of the second accommodating unit 601 to the vacuum pump 635. At an intermediate portion of the third passage 788 is mounted a third valve 720.

The first accommodating unit 600 is provided with a first accommodation state detector 612 such as a liquid surface detector. The detector 612 is designed to detect the liquid surface of the materials as they rise to a position indicated by "A1".

In the second accommodating unit 601 is mounted a second level detector 622. This detector 622 detects the liquid surface of the removed materials 34 when it reaches a position as indicated by "B1."

A fourth passage 888 communicates the vacuum pump 635 with the first accommodating unit 600.

Pressure Reducing Unit 630

The pressure reducing unit 630 reduces the pressure within the first accommodating unit 600 to a constant vacuum pressure and, as necessary, also reduces the pressure within the second accommodating unit 601. The pressure reducing unit 630 includes the vacuum pump 635, the third valve 720, the third passage 788 and the fourth passage 888.

Pressure Detecting Unit 611

The pressure detecting unit 611 is a pressure sensor. The pressure detecting unit 611 detects the inner pressure of the first accommodating unit 600.

Pressure Adjusting Unit 590

The pressure adjusting unit 590 includes a cylindrical portion 594, a member 591, and a driving source (not shown). The cylindrical portion 594 projects from the top lid of the first accommodating unit 600. The member 591 adjusts the size of opening 596 by operating the driving source and, as a result, the amount of the air entering through the opening 596.

Figure 11:
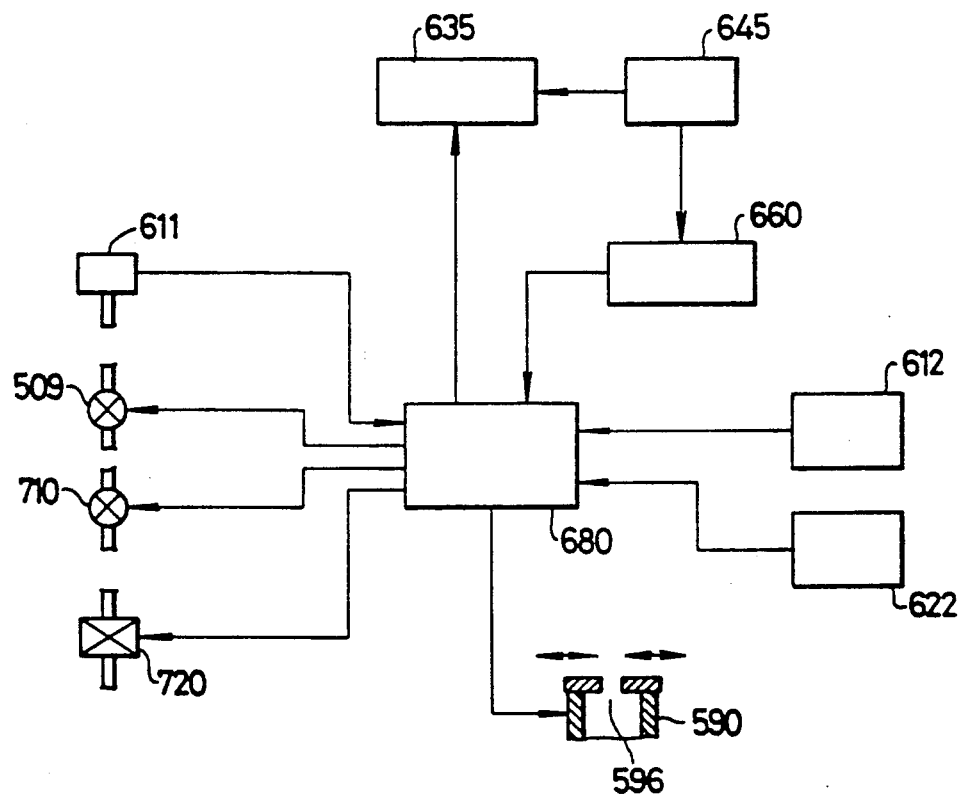
FIG. 11 is a diagram showing a control system of Example 7.

The pressure controlling unit 680 of FIG. 11 is provided with a signal from the pressure detecting unit 611, a signal from an operating unit 660 such as a foot switch or the like, and signals from the first and second accommodation level detectors 612 and 622, respectively.

The pressure controlling unit 680 can adjust the size of the opening 596 of the pressure adjusting unit 590 on the basis of the signal from the pressure detecting unit 611. The pressure controlling unit 680 further provides operation signals for operating the vacuum pump 635 and the first, second and third valves 509, 710 and 720, respectively. The vacuum pump 635, the operation unit 660 and the like are connected to an electric source 645.

OPERATION

The operation will be described with reference to FIGS. 10 and 11.

Figure 10:
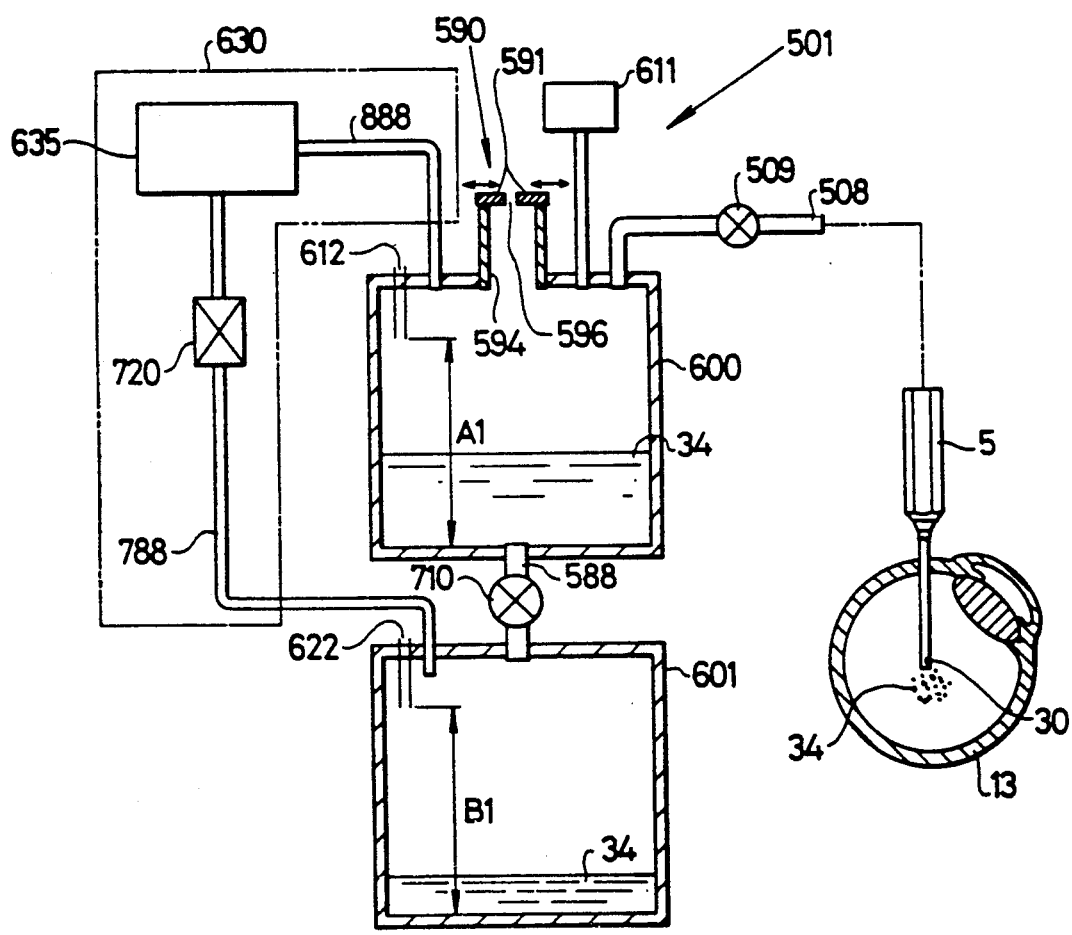
FIG. 10 is a view showing Example 7.

As the electric source 645 is turned on, the vacuum pump 635 starts operating to evacuate the first accommodating unit 600 to vacuum through the fourth passage 888 of FIG. 10. At this time, the first valve 509 is closed and the second valve 710 is also closed while the third valve 720 is open and the member 591 of the pressure adjusting unit 590 becomes full open.

As the foot switch of the operating unit 660 is turned on, suction starts. At this time, the first valve 509 is opened while the second valve 710 and the third valve 720 are closed. The size of the opening 596 of the pressure adjusting unit 590 is changed to adjust the pressure within first accommodating unit 600 so as to correspond to the pressure (a given pressure) as indicated by the foot switch of the operating unit 660 while detecting the pressure by the pressure detecting unit 611. The removed materials 34 enter the first accommodating unit 600 through the first passage 508 from the aspirating mouth portion 30.

Before the amount of the removed materials 34 in the first accommodating unit 600 reaches the level as indicated by "A1", the foot switch is turned off (to stop aspirating), thereby closing the first valve 509 while opening the second and third valves 710 and 720 and fully opening the opening 596 of the pressure adjusting unit 590.

The removed materials 34 are transferred to the second accommodating unit 601 from the first accommodating unit 600 through the second passage 588.

If the foot switch is turned on while the removed materials 34 are being transferred, aspiration starts again and operation of the above procedures is repeated.

It is to be noted that, when the amount of the removed materials 34 within the first accommodating unit 600 reaches the level as indicated by "A1" as aspiration proceeds, a state is forcibly continued for a set period of time, in which the first valve 509 is closed as well as the second valve 710 and the third valve 720 are opened and the opening 596 of the pressure adjusting unit 590 becomes full open, thus transferring the removed materials 34 within the first accommodating unit 600 to the second accommodating unit 601.

When the set period of time has passed, an aspiration operation can be resumed by turning the foot switch on. As aspiration further proceeds, the amount of the removed materials 34 within the second accommodating unit 601 reaches a level as indicated by "B1", then the second and third valves 710 and 720, respectively, are forcibly closed.

The removed materials 34 reach both the A1 level of the first accommodating unit 600 and the B1 level of the second accommodating unit 601 as aspiration is carried over a long period of time. Then the first, second and third valves 509, 710 and 720, respectively, are forcibly closed while the opening 596 of the pressure adjusting unit 590 becomes full open, whereby aspiration is suspended.

In Example 7, in place of setting such a period of time, it is also possible that aspiration operation can be resumed at the time when the liquid surface of the removed materials 34 is lowered to a given level.

Example 8

Figure 12:
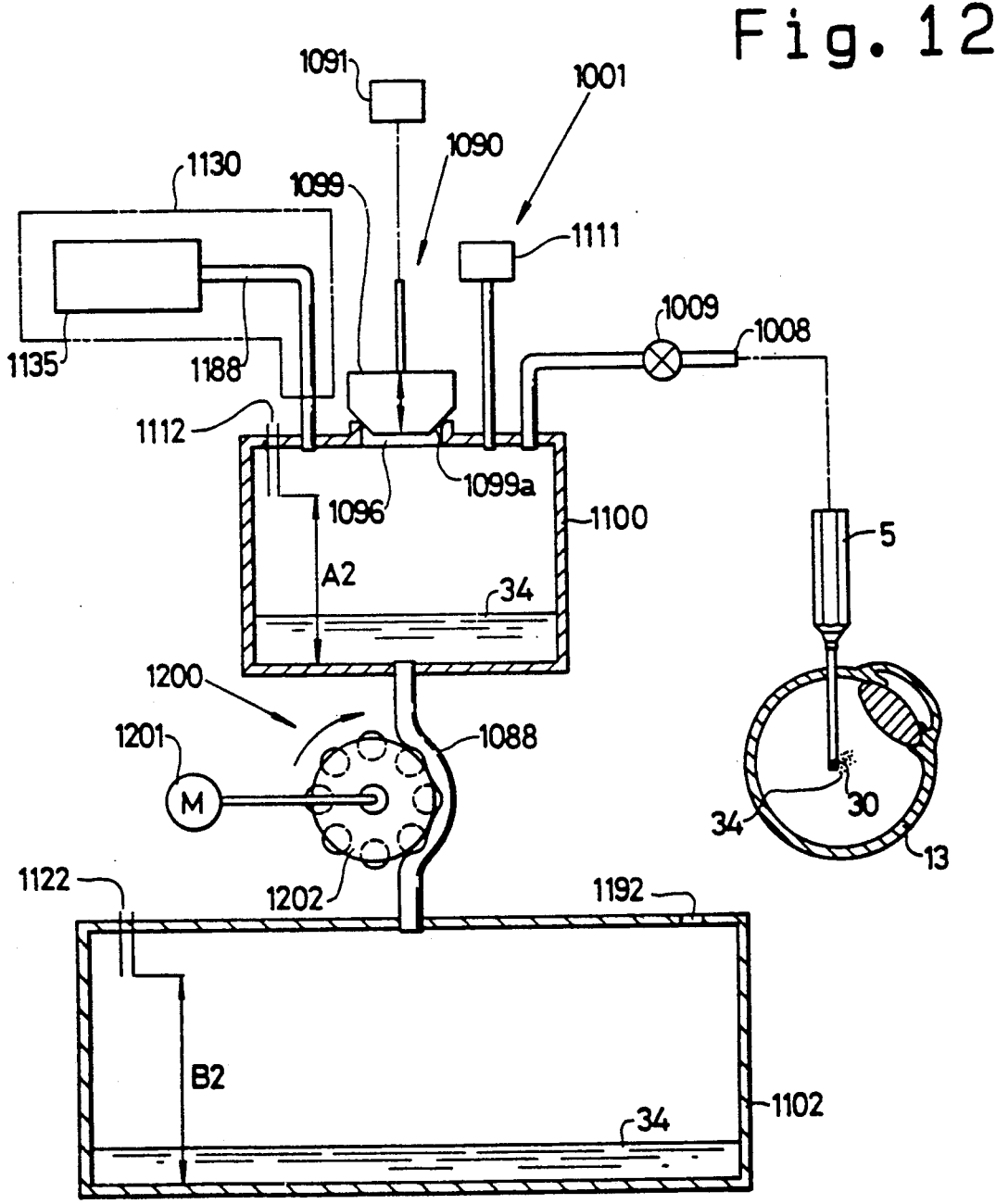
FIG. 12 is a view showing Example 8.

This example will be described with reference to FIG. 12.

An aspirator 1001 is a device capable of aspirating the materials 34 to be removed the eyeball 13 by means of negative pressures.

Accommodating Units 1100 & 1102

The aspirator 1001 includes first and second accommodating units 1100 and 1102, respectively, each in the form of a bottle. Each of the accommodating units 1100 and 1102 is to accommodate the removed materials 34. The second accommodating unit 1102 has a capacity larger than the first accommodating unit 1100.

The aspirating mouth portion 30 of the cutter 5 communicates with a first passage 1008 which, in turn, reaches the inside of the first accommodating unit 1100 through the top lid of the first accommodating unit 1100. A valve 1009 is mounted at an intermediate portion of the first passage 1008.

A second passage 1088 communicates with the inside of the second accommodating unit 1102 through a top lid thereof from a bottom lid of the first accommodating unit 1100. At an intermediate portion of the second passage 1088 is mounted a squeezing roller device 1200. The roller device 1200 comprises a motor 1201 and a roller 1202. The roller may be of conventional type.

A third passage 1188 is communicated with a vacuum pump 1135 from the top lid of the first accommodating unit 1100.

The first accommodating unit 1100 is provided with a first accommodation state detector 1112 such as a liquid surface detector. The detector 1112 detects the liquid surface level of the removed materials 34 as the materials 34 come to a level as indicated by "A2".

The second accommodating unit 1102 is provided with a second accommodation state detector 1122. The second detector 1122 is to detect a liquid surface level of the removed materials 34 as they come to a level as indicated by "B2".

The second accommodating unit 1102 is further provided with a hole 1192 passing therethrough to the air.

Pressure Reducing Unit 1130

The pressure reducing unit 1130 is to reduce the pressure within the first accommodating unit 1100 always at a constant vacuum pressure. The pressure reducing unit 1130 includes the vacuum pump 1135 and the third passage 1188.

Pressure Detecting Unit 1111

The pressure detecting unit 1111 is a pressure sensor. The pressure detecting unit 1111 detects the inner pressure of the first accommodating unit 1100.

Pressure Adjusting Unit 1090

The pressure adjusting unit 1090 comprises a hole 1096 of the first accommodating unit 1100 and a member 1099 composed of an elastic material. The member 1099 is provided with a tapered portion 1099a. The tapered portion 1099a adjusts the size of the opening 1096. The member 1099 is movable in both upward and downward directions by means of a mechanism unit 1091.

Figure 13:
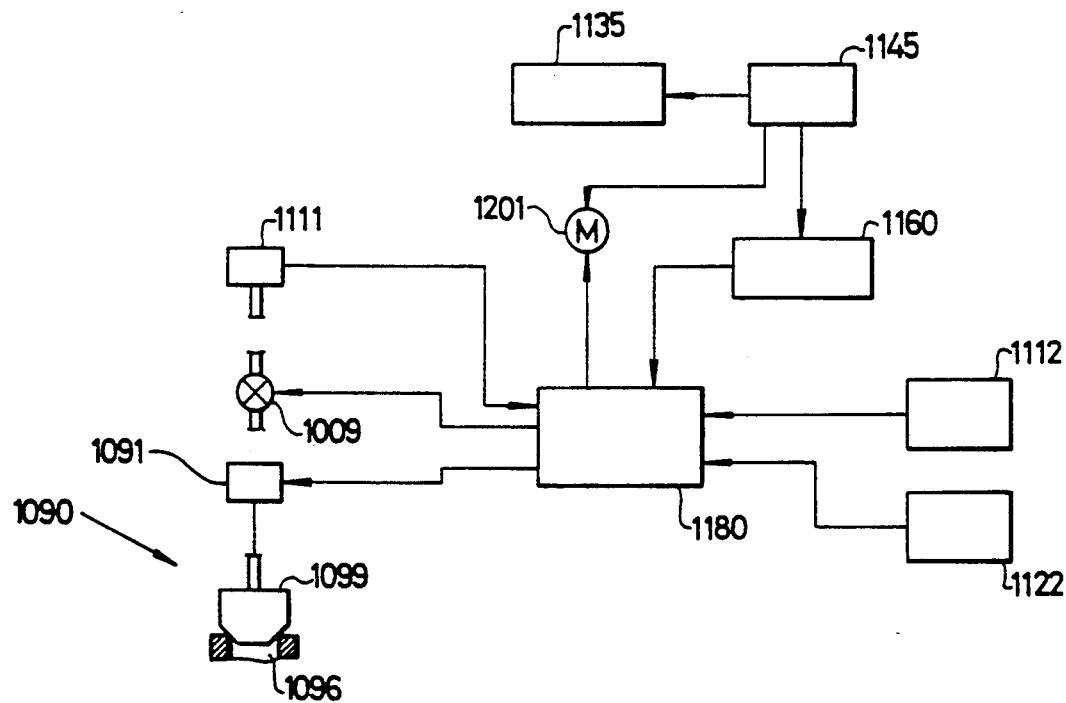
FIG. 13 is a diagram showing a control system for Example 8.

To the pressure controlling unit 1180 of FIG. 13 is given a signal from the pressure detecting unit 1111, a signal from an operating unit 1160 such as a foot switch or the like, and signals from the first and second accommodation state detectors 1112 and 1122, respectively.

The pressure controlling unit 1180 operates the mechanism unit 1091 on the basis of the signal from the pressure detecting unit 1111, thereby adjusting the size of the opening 1096 of the pressure adjusting unit 1099. The pressure controlling unit 1180 generates operation signals to the vacuum pump 1135, the valve 1009, and the motor 1201.

The vacuum pump 1135, the operating unit 1160, and the motor 1201 are connected to an electric source 1145.

OPERATION

As the electric source is turned on, the vacuum pump 1135 starts operating. The first accommodating unit 1100 is reduced to vacuum through the third passage 1188. The valve 1009 is closed and the opening 1096 of the pressure adjusting unit 1090 is fully opened. The rollers 1202 are rotated by means of the motor 1201.

The first accommodating unit 1100 is at atmospheric pressure. As the foot switch of the operating unit 1160 is turned on, aspiration starts. The valve 1009 is opened and the size of the opening 1096 of the pressure adjusting unit 1090 is altered so as to amount to a pressure (a given pressure) indicated on the foot switch while detecting the pressure within the first accommodating unit 1100 by means of the pressure detecting unit 1111.

The materials 34 to be removed are held in the first accommodating unit 1100 from the aspirating mouth portion 30 through the first passage 1008. At the same time, as the squeezing rollers 1202 are rotating, the removed materials 34 are transferred to the second accommodating unit 1102 from the first accommodating unit 1100 through the second passage 1088. At this time, as the foot switch is turned off, the valve 1009 is closed and the opening 1096 is fully closed, thereby suspending aspiration.

An amount of the removed materials 34 to be squeezed by means of the squeezing rollers 1202 during aspiration is determined in advance such that the amount of the removed materials 34 to be transferred from the first accommodating unit 1100 to the second accommodating unit 1102 by means of the squeezing rollers 1202 becomes larger than the amount of the removed materials 34 to be accommodated in the first accommodating unit 1100.

When the liquid surface of the removed materials 34 within the first accommodating unit 1100 reaches a level as indicated by "A2" on account of failure of the device or for other reasons, the first accommodation state detector 1112 is turned on to forcibly close the valve 1009, fully open the opening 1096 and stop operation of the motor 1201 rotating the squeezing rollers 1202, suspending aspiration and giving an alarm.

When the liquid surface of the removed materials within the second accommodating unit 1102 reaches a level B2 during aspiration, the second accommodation state detector 1122 is turned on, closing forcibly the valve 1009, opening fully the opening 1096, and stopping operation of the motor 1201 rotating the squeezing rollers 1202, thereby suspending the aspiration.

Fluctuations in pressures within the first accommodating unit 100 using the squeezing rollers can be avoided by means of the pressure adjusting unit 1090.

It is also possible to turn on o off the motor 1201 for the squeezing rollers by connecting it to the foot switch or to change the number of its revolutions in combination with the pressure as indicated by the foot switch.

As have been described hereinabove, the present invention permits an easy adjustment of pressures within the accommodating units merely by controlling the size of the opening of the pressure adjusting unit. This can simplify the structure and miniaturize the size of the aspirator.

Example 9

Figure 14:
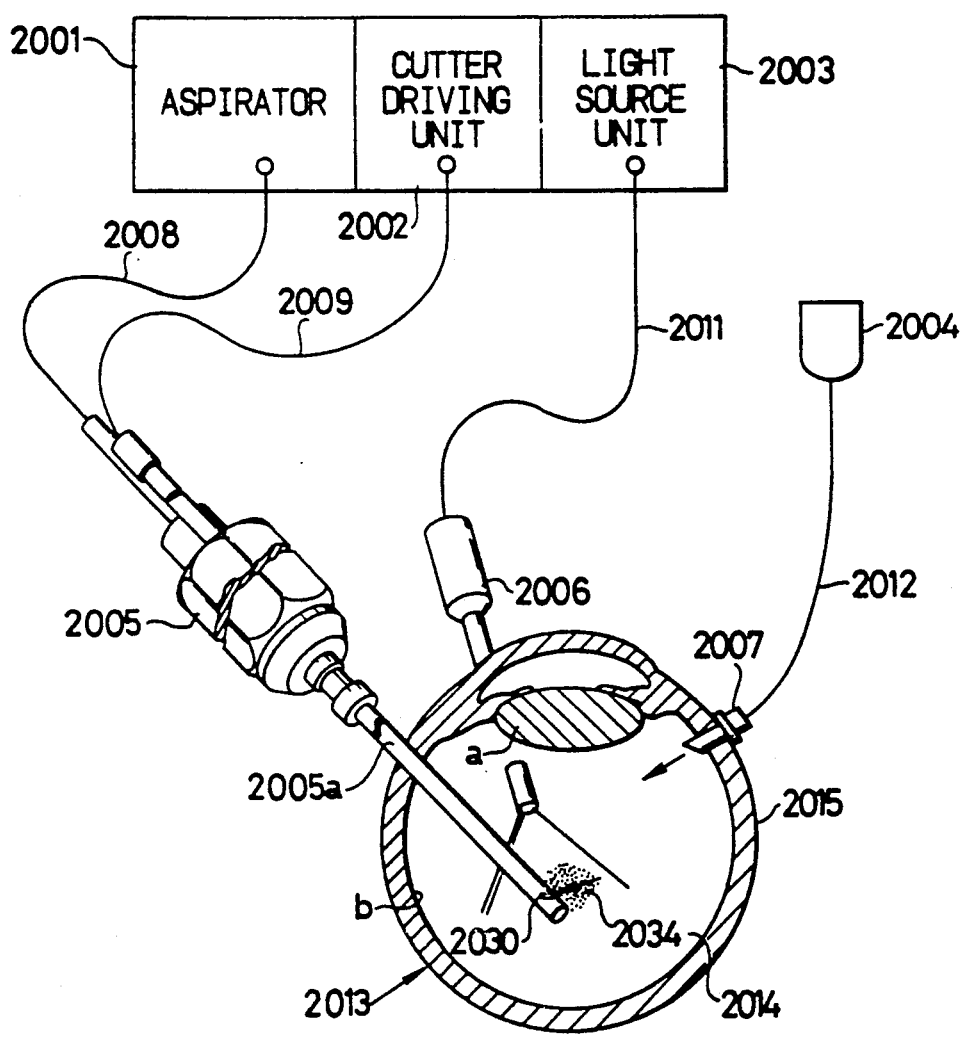
FIG. 14 is a view showing a vitreous body surgery device equipped with the aspirator according to the present invention.

As shown in FIG. 14, the aspirator 2001 according to the present invention is mounted in a surgery apparatus for the vitreous body as one example.

In the surgery of the vitreous body, for example, an unclear portion of the vitreous body 2014 in a gel form (referred to herein as "removed material 2034" and related terms) between the lens a and the retina b is removed by suction and replaced by a clear liquid. This enables light to reach the retina b through the lens a, thus recovering one's sight.

A vitreous body surgery apparatus comprises the aspirator 2001, a cutter driving unit 2002, a light source unit 2003, an infusion bottle 2004, a cutter 2005 with a suction mechanism, a light guide 2006, and an infusion plug 2007.

The cutter 2005 contains an insert portion 2005a. The insert portion 2005a is to insert it into the eyeball 2013 through the sclera 2015 of the eyeball 2013. At the tip portion of the insert portion 2005a is provided an aspirating mouth portion 2030. The cutter 2005 is designed to cut the materials 2034 which are inserted into its aspirating mouth portion 2030 and the cut materials 2034 are sucked into the aspirator 2001 through the inside of the insert portion 2005a and a first passage 2008.

To the cutter driving unit 2002 is connected a tube 2009 for compressed air. Through the tube 2009 is fed compressed air to the cutter 2005 and the compressed air operates the cutter 2005 to cut and remove the materials 2034. The light source unit 2003 emits light to the light guide 2006 through an optical fiber 2011. A tip portion of the light guide 2006 is inserted into the eyeball 2013 and the light guide 2006 can provide a portion around the aspirating mouth portion 2030 with light.

The infusion bottle 2004 accommodates an infusion. The infusion is supplied to the inside of the eyeball 2013 through an infusion tube 2012 and the infusion plug 2007. The infusion fills in the eyeball 2013 in order to replace the removed materials 2034 which have been cut and removed by suction, thereby recovering one's sight.

Aspirator 2001

The aspirator 2001 will be described more in detail with reference to FIG. 15.

The aspirator 2001 is a device to aspirate the materials 2034 to be removed from the eyeball 2013 by means of a negative pressure.

Accommodating Units 2100–2102 and Air Reservoir 2300

The aspirator 2001 contains first, second and third accommodating units 2100–2102, respectively, each in a bottle form, and an air reservoir 2300. The accommodating units 2100–2102 accommodate the removed materials 2034. The first and second accommodating units 2100 and 2101 have substantially the same capacities, and the third accommodating unit 2102 has a capacity larger than each of those units.

The aspirating mouth portion 2030 of the cutter 2005 is provided at its inside with a first passage 2008 and the first passage 2008 extends so as to pass through a top lid of the first accommodating unit 2100 to the inside thereof.

A second passage 2088 leads from the bottom of the first accommodating unit 2100 to the inside of the second accommodating unit 2101 through the top lid thereof. At an intermediate portion of the second passage 2088 is mounted a first valve 2210.

A third passage 2188 is led from the bottom of the second accommodating unit 2101 through the top lid of the third accommodating unit 2102 to the inside of the third accommodating unit 2102. From the top lid of the second accommodating unit 2101 is led a fourth passage 2330 to the air reservoir 2300.

The first accommodating unit 2100 is provided with first and second accommodation state detector, 2112 and 2113 respectively, such as a liquid surface detector. These detectors detect the liquid surface of the removed materials 2034 as it comes to a liquid surface level as indicated by "A" and "B", respectively.

The second accommodating unit 2101 is provided with a third accommodation state detector 2123 which can detect the liquid surface of the removed materials 2034 as it comes to a liquid surface level "C".

The third accommodating unit 2102 is provided with a fourth accommodation state detector 2123 which can detect the liquid surface of the removed materials 2034 as it comes to a liquid surface level "D".

First Pressure Adjusting Unit 2070

The first pressure adjusting unit 2070 includes a vacuum pump 2130, a pipe 2120, a valve 2121, a pressure sensor 2111 and a lid 2106.

The pressure sensor 2111 measures the pressure within the first accommodating unit 2100. The vacuum pump 2130 reduces the pressure within the first accommodating unit 2100 through the pipe 2120. The valve 2121 is disposed at an intermediate portion of the pipe 2120.

The first accommodating unit 2100 is provided with a hole 2100b. To the hole 2100b is pressed the lid 2106.

The lid 2106 is mounted on one end of a level 2104a. The other end of the level 2104a is mounted to a shaft 2104c. A solenoid 2104 is mounted to a fixed portion 2104d. The shaft 2104c of the solenoid 2104 is pulled in a direction toward a fixed portion 2104e by means of a spring 2105.

Second Pressure Adjusting Unit 2340

The second pressure adjusting unit 2340 is disposed at the air reservoir 2300. The second pressure adjusting unit 2340 includes a vacuum pump 2310, a compression pump 2320, valves 2321, 2322, 2323, pipes 2324, 2325, 2326, and a pressure sensor 2315.

The vacuum pump 2310 for reducing pressures is connected through the pipe 2324 to the air reservoir 2300. The compression pump 2320 for increasing pressures is connected through the pipe 2325 to the air reservoir 2300. At an intermediate portion of the pipe 2324 is mounted valve 2321. At an intermediate portion of the pipe 2325 is mounted the valve 2322. To the pipe 2326 is mounted the valve 2323. An end of the pipe 2326 is exposed to the air. The pressure sensor 2315 measures pressures within the air reservoir 2300 and within the second accommodating unit 2101.

Control System

Figure 16:
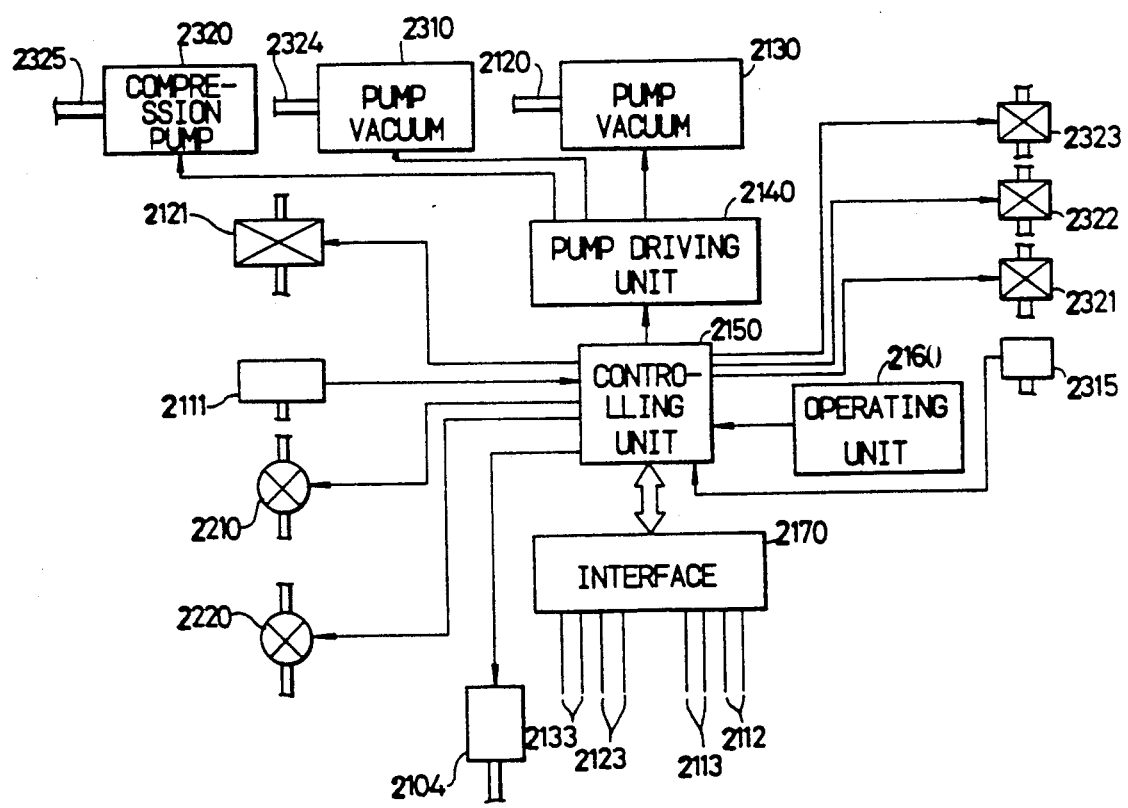
FIG. 16 is a diagram showing a control system.

The control system will be described with reference to FIG. 16.

To a controlling unit 2150 ar electrically connected the valves 2121, 2321, 2322, 2323, pressure sensors 2111, 2315, first valve 2210, second valve 2220, and solenoid 2104.

The controlling unit 2150 is connected to an operating unit 2160. To the controlling unit 2150 are fed pressures detected from the pressure sensors 2111 and 2315. To the controlling unit 2150 is connected an interface 2170. To the interface 2170 are connected first, second, third and fourth accommodation state detectors 2112, 2113, 2123, and 2133, respectively. To the interface 2170 is fed a signal indicating a liquid surface level of the materials to be removed.

The vacuum pumps 2130 and 2310 and the compression pump 2320 receive an instruction from the controlling unit 2150 through a pump driving unit 2140.

Surgery of Vitreous Body

Description will be made with reference to FIG. 15.

An electric source is turned on and the vacuum pumps 2130 and 2310 are turned on and at the same time the compression pump 2320 is also turned on.

The first valve 2121 is closed and the lid 2106 is opened (because the solenoid 2104 is turned off). The valve 2321 is closed, the valve 2323 is opened and the valve 2322 is closed. The first valve 2210 and the second valve 2220 are opened.

As the foot switch of the operating unit 2160 of FIG. 3 or the like is turned on as a signal to indicate the start of aspiration, the valve 2121 is opened, the lid 2106 is closed, the first valve 2210 is closed, the second valve 2220 is closed, the valve 2321 is opened, and the valve 2323 is closed.

This operation makes the pressure within the first accommodating unit 2100 a negative pressure. Materials 2034 in the eyeball 2013 to be removed are led from the aspirating mouth portion 2030 through the first passage 2008 to the first accommodating unit 2100.

When the pressure sensor 2111 detects that the pressure within the first accommodating unit 2100 has reached a given pressure during aspiration, the valve 2121 and the lid 2106 are closed.

If the pressure sensor 2111 has detected that the pressure within the first accommodating unit 2100 becomes higher than the given pressure, the valve 2121 is opened and the lid 2106 is closed. If the pressure sensor 2111 has detected pressure lower than the given pressure, the valve 2121 is closed and the lid 2106 is opened.

The pressure within the second accommodating unit 2101 is detected by means of the pressure sensor 2315. If the pressure of the second accommodating unit 2101 reaches a given pressure (equal to or slightly lower than the pressure within the first accommodating unit 2100), the valve 2321 is closed (while the valve 2323 is kept on being closed). If the pressure sensor 2315 detects that the pressure within the second accommodating unit 2101 becomes higher than the given pressure, the valve 2321 is opened (while the valve 2323 is kept closed). If the pressure sensor 2315 detects a pressure lower than the given pressure, the valve 2321 is closed and the valve 2323 is opened.

When the first accommodation state detector 2112 detects the fact that the amount of the removed materials 2034 within the first accommodating unit 2100 has reached the level "A", the first valve 2210 is opened. The removed materials 2034 within the first accommodating unit 2100 are then transferred through the second passage 2088 to the second accommodating unit 2101. When the second accommodation state detector 2113 detects the fact that the amount of the removed materials 2034 within the first accommodating unit 2100 has reached the level "B", the second valve 2210 is closed.

After the second valve 2210 is closed, the valve 2321 of the second pressure adjusting unit 2340 is closed, the valve 2323 is closed, and the valve 2322 is opened to lead the compressive air to the inside of the second accommodating unit 2101 through the air reservoir 2300. The third valve 2220 is also opened.

The removed materials 2034 within the second accommodating unit 2101 are caused to be positively transferred to the third accommodating unit 2102 through the third passage 2188 by means of the compressed air fed through the air reservoir 2300. If the third accommodation state detector 2123 detects the fact that the removed materials 2034 within the second accommodating unit 2101 reach the level "C", the valve 2322 is closed and the second valve 2220 is closed. In order to reduce the second accommodating unit 2101 to vacuum again, the valve 2323 is closed and the valve 2321 is opened.

It is to be noted, however, that, as the first accommodating unit 2100 is kept reduced to a set value during a period of time up to this procedure, the materials 2034 within the eyeball 2013 can be continuously directed to the first accommodating unit 2100 from the aspirating mouth portion 2030 through the first passage 2008.

After these procedures have been repeated, the foot switch or the like is turned off to conclude the aspiration. If the aspiration is continued and the removed materials within the third accommodating unit 2102 reach the level "D", the aspiration is forcibly suspended and such is displayed.

Example 10

Figure 17:
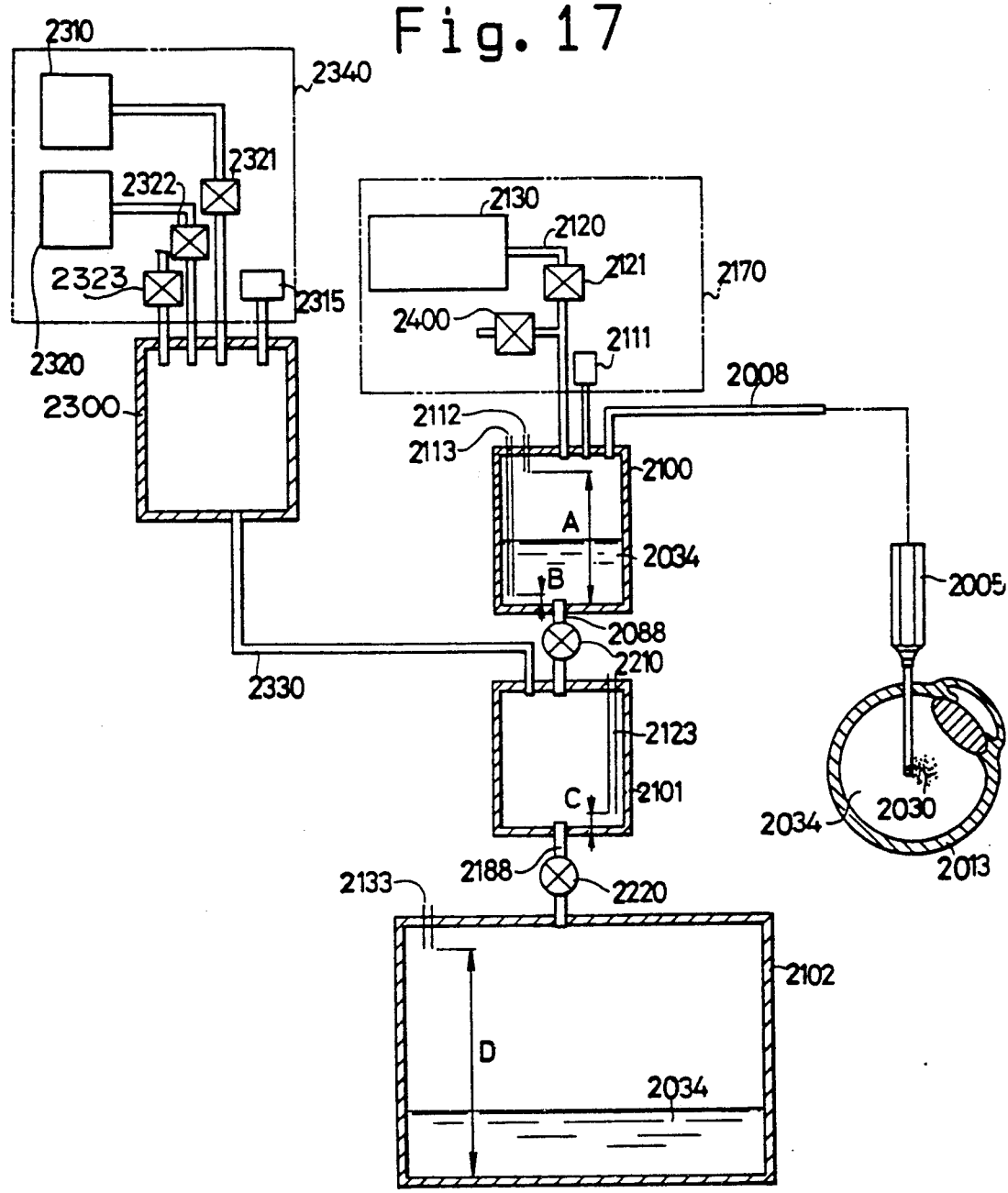
FIG. 17 is a view showing Example 10.

This example will be described with reference to FIG. 17.

Figure 15:
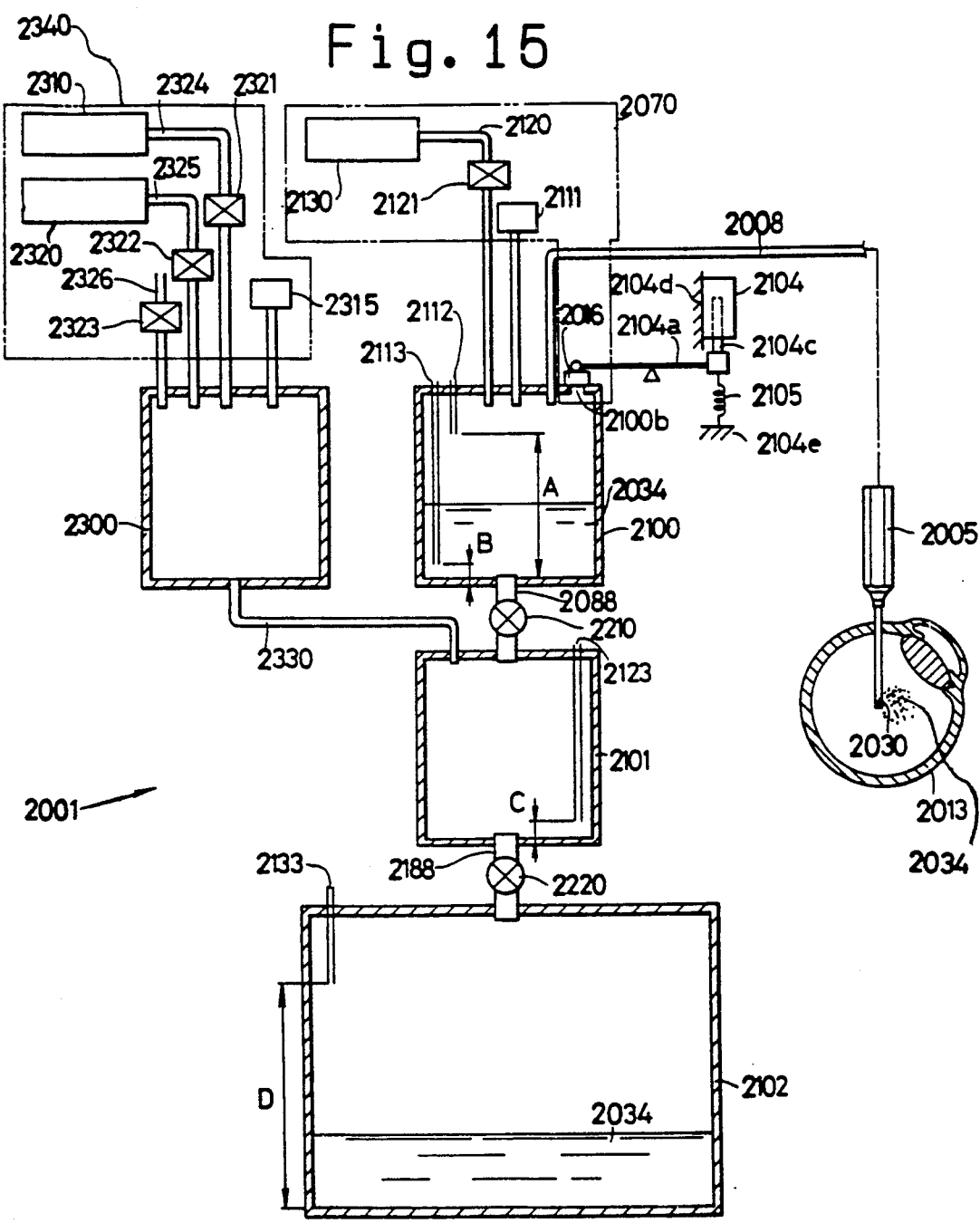
FIG. 15 is a view showing Example 9 according to the present invention.

What is different from Example 9 of FIG. 15 is that a valve 2400 is disposed in place of the lid 2106 of Example 9 and its surrounding portion. The valve 2400 is mounted at an intermediate portion of the pipe 2120 and is to expose the inside of the first accommodating unit 2100 to the air.

The valve 2400 serves as part of the first pressure adjusting unit 2170. Description on the other portions will be omitted herefrom because they are the same as in Example 1.

It is to be noted herein that the present invention is not restricted to the above examples. It is thus to be understood that each of the accommodating units may be in a cylindrical form or in any other form. The third accommodating unit may be a flexible container. The third accommodating unit may be a closed type as shown in FIGS. 15 and 17 or in a form in which its part is exposed to the air. Furthermore, it may be a bucket having no top lid and may be merely placed so a to receive the removed materials from the third passage.

The pressure adjusting unit 2070 may be a unit capable of adjusting pressures using a vacuum pump and a compression pump. In place of the vacuum pump, there may be used a device to create vacuum from the compressive air.

The accommodation state detector may be a non-contact type sensor as well as a contact type sensor. A flowmeter may be used for this purpose.

In place of the second accommodation state detector 2113, a timer may be used which counts the time required to allow a predetermined amount of the removed materials to drop.

In place of the fourth accommodation state detector 2133, there may be employed one such that accommodation of a predetermined amount of the removed materials can be presumed from a specified number of openings of the third valve 2220 by counting the number of its openings. If the third accommodating unit is large enough, it is not necessarily required to mount the fourth accommodation state detector 2133. The second and third valves 2210 and 2220, respectively, may be each a balloon or the like. By changing a size of the balloon, the pipe may be closed or opened.

In place of the third accommodation state detector 2123, the amount of the removed materials within the accommodating unit may be controlled by means of time.

In the examples as have been described hereinabove, although the vacuum pump is separately used in the first and second pressure adjusting units, one vacuum pump may be shared by them.

As the pressure of the compressed air from the compression pump 2320 is sufficient, there may be disposed a regulator or a small hole between the compression pump and the air reservoir.

In the above-mentioned examples, the compression pump 2320 and the pressure sensor 2315 may be connected directly to the second accommodating unit 2101.

Without using the compression pump, the removed materials may be designed to drop by means of their own weight from the second accommodating unit onto the third accommodating unit The second pressure adjusting unit 2340 may be disposed directly at the second accommodating unit without passage through the air reservoir.

The accommodation state detector may be of the type as will be described hereinbelow.

Figure 18:
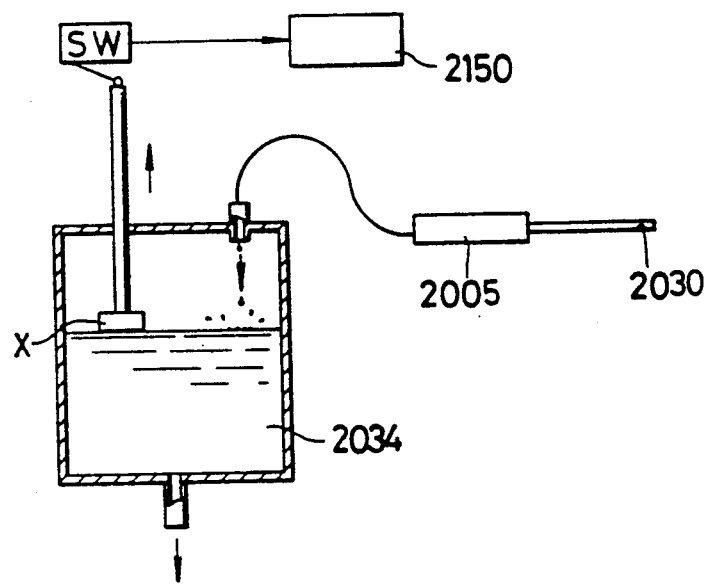
FIG. 18 is a view showing a variation of a level detecting unit.

(A) As shown in FIG. 18, a floating material X may be used. Using a force of the floating material X left suspended by means of the removed materials 2034, a microswitch or a lead switch SW may be turned on or off.

(B) Using light, the amount of the removed materials accommodated may be checked by means of light refraction, reflection, a change of luminous energy or the like.

(C) The amount of the removed materials accommodated may be check by means of a variation in weights.

In the above-mentioned examples, the lid of the first pressure adjusting unit 2070 may be opened or closed by means of the solenoid. However, the lid may be opened or closed by means of a motor or the like.

As only the first and second accommodating units of smaller capacities may be set at a given pressure required for aspiration, the time required for suction may be shortened compared with the time to be required for suction of the accommodating unit of a larger capacity.

Example 11

Figure 19:
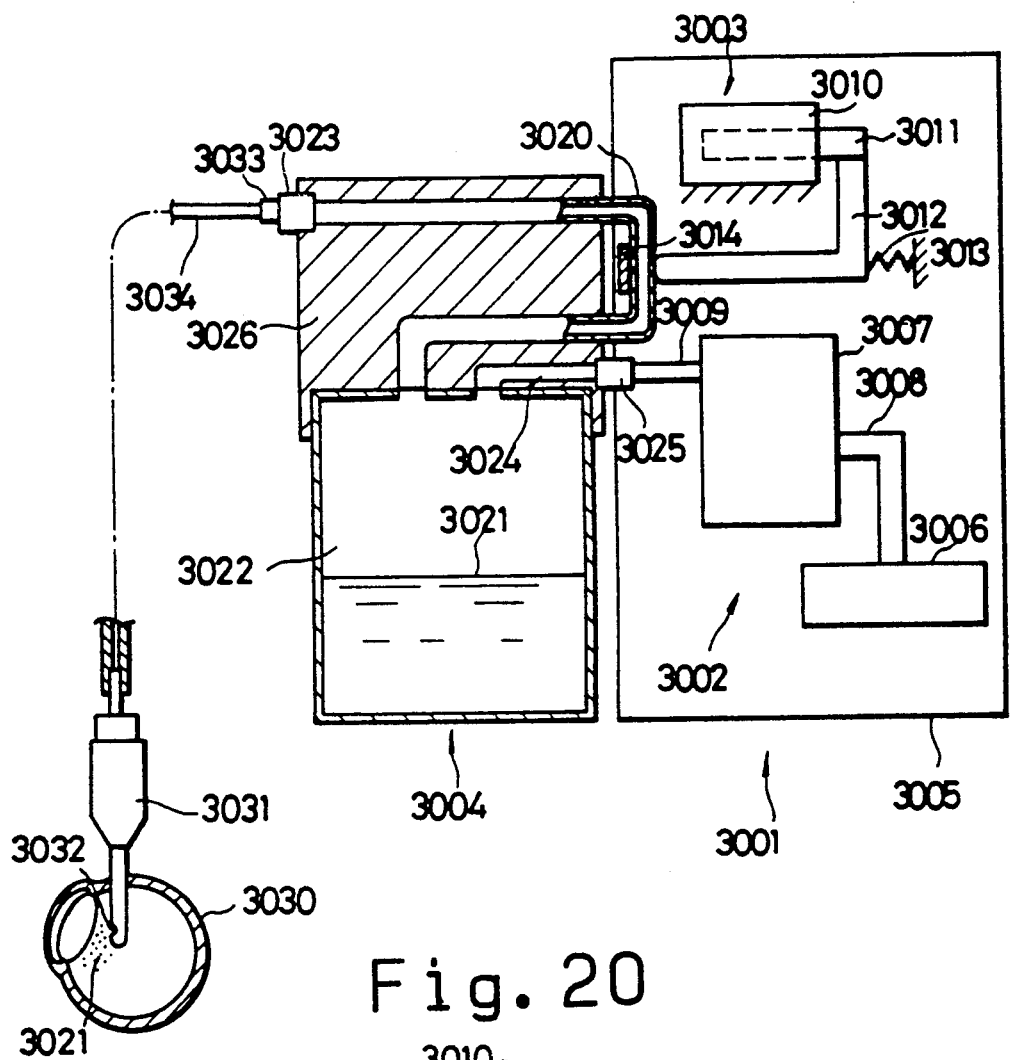
FIG. 19 is a view showing Example 11 according to the present invention.

FIG. 19 shows an aspirator of Example 11 according to the present invention. The aspirator 3001 comprises a vacuum controlling unit 3002, a materials-passage opening/closing unit 3003, a main body 3005 of the aspirator 3001, and one aspirating cassette 3004 mounted detachably on the main body 3005.

The vacuum controlling unit 3002 and the materials-passage opening/closing unit 3003 are disposed within the main body 3005.

Vacuum Controlling Unit

The vacuum controlling unit 3002 includes a vacuum pump 3006, a pressure adjusting unit 3007, a passage 3008, and a passage 3009. The passage 3008 is interconnected to the vacuum pump 3006 and the pressure adjusting unit 3007 and feeds reduced air from the vacuum pump 3006 to the pressure adjusting unit 3007. The pressure adjusting unit 3007 produces air having a set pressure by means of an instruction from a pressure setting unit (for example, a foot switch (not shown)). The passage 3009 is open at its one end and is connected at its other end to the pressure adjusting unit 3007 in order to feed the air of given pressure produced by the pressure adjusting unit 3007 to its open end.

Materials-Passage Opening/Closing Unit

The materials-passage opening/closing unit 3003 includes a solenoid 3010, an iron core 3011, an L-shaped arm 3012, a spring 3013, and a Stopper 3014.

The iron core 3011 is inserted in the solenoid 3010 and is disposed so as to be pulled into the solenoid 3010 as the solenoid 3010 is turned on. To the iron core 3011 is mounted the L-shaped arm 3012 and the L-shaped arm 3012 is always urged by means of the spring 3013 in a direction in which the iron core 3011 is pulled out of the solenoid 3010.

A flexible tube 3020 of the aspirating cassette 3004 is disposed between the stopper 3014 and the L-shaped arm 3012 and, as the solenoid 3010 is turned on by means of a signal, the iron core 3011 is pulled into the solenoid 3010 and, at the same time, it causes the L-shaped arm 3012 to press the flexible tube 3020.

Figure 20:
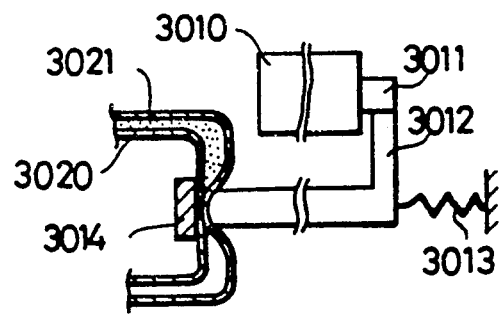
FIG. 20 is a view showing the flexible tube of Example 11 in a closed state.

This arrangement enables a closure of passage of the removed materials 3021 through the flexible tube 3020 by squeezing the flexible tube 3020 by means of the L-shaped arm 3012 and the stopper 3014 as shown in FIG. 20.

As a signal is given to release the closure, the L-shaped arm 3012 and the iron core 3011 are forcibly returned to their original positions by means of the spring 3013, thus allowing passage of the removed materials 3021 through the flexible tube 3020.

As has been described hereinabove, the materials-passage opening/closing unit 3003 opens or closes a passage of the removed materials 3021 within the flexible tube 3020 of the aspirating cassette 3004 through the flexible tube 3020.

Aspirating Cassette

The aspirating cassette 3004 comprises a bottle 3022, an aspirating mouth portion 3023, the flexible tube 3020, a tube 3024, a connecting portion 3025 and a bottle head 3026. The aspirating cassette 3004 is mounted detachably to the main body 3005 of the aspirator 3001. As the aspirating cassette 3004 is mounted to the main body 3005, part of the flexible tube 3020 is located at a position interposed between the stopper 3014 and the L-shaped arm 3012 of the materials-passage opening/closing unit 3003 and the connecting portion 3025 is connected to the open end of the passage 3009 of the vacuum controlling unit 3002.

Bottle

The bottle 3022 accommodates the removed materials 3021 and is interconnected to each one end of the flexible tube 3020 and the tube 3024. To the other end of the tube 3024 is connected the connecting portion 3025 to pass vacuum adjusted by the vacuum controlling unit 3002 and convey it to the bottle 3022. To the other end of the flexible tube 3020 is connected the aspirating mouth portion 3023. The aspirating mouth portion 3023 is connected to the cutter 3031 located within the eyeball 3030 through a connector 3033 and a line 3034. The cutter 3031 is provided with the aspirating mouth 3032 through which the removed materials 3021 are aspirated from the eyeball 3021. The removed materials 3021 may be, for example in the form of an unclear vitreous body.

Although the bottle 3022 is closed by means of the bottle head 3026, the bottle head 3026 is detachable. The tube 3024 and the flexible tube 3020 are disposed in this bottle head 3026.

Operation of Aspiration

The operation of aspiration will be described with respect to FIGS. 19 and 20.

The aspirating cassette 3004 is mounted o the main body 3005 of the aspirator 3001 and the connector 3033 of the cutter 3031 is attached to the aspirating mouth portion 3023 of the aspirating cassette 3004. As an electric source of the main body is turned on, the vacuum pump 3006 is turned on and the solenoid 3010 of the materials-passage opening/closing unit 3003 is also turned on to squeeze the flexible tube 3020 of the aspirating cassette 3004.

As the foot switch or the like is turned on and aspiration starts, reduced air arranged by means of the pressure adjusting unit 3007 is fed through the passage 3009 to the bottle 3022. At the same time, the solenoid 3010 is turned off to allow passage through the flexible tube 3020. The removed materials 3021 in the eyeball 3030 are then sucked from the aspirating mouth 3032 of the cutter 3031 and conveyed to the bottle 3022 through the tube 3034, the connector 3033, the aspirating mouth portion 3023 and the flexible tube 3020.

In order to suspend aspiration, the foot switch or the like is turned off, thereby turning the pressure adjusting unit 3007 to atmospheric pressure and feeding the atmospheric pressure to the bottle 3022 and, at the same time, turning the solenoid 3010 on to squeeze the flexible tube 3020 to thereby close the passage of the removed materials 3021 therethrough and suspend the aspiration.

When a detector (not shown) detects the fact that the bottle 3022 is filled with the removed materials 3021, the solenoid 3010 is forcibly turned on to squeeze the flexible tube 3020 regardless of the state in which the foot switch or the like is turned. At the same time, the bottle 3022 is turned to atmospheric pressure by means of the vacuum controlling unit 3002, thereby suspending aspiration forcibly.

As has been described hereinabove, passage or suspension of the passage of the remove materials 3021 can be carried out within the main body 3005 without applying force to the bottle 3022 and the bottle head 3026. Accordingly, no risk is incurred that the aspirating cassette 3004 will be detached from the main body 3005.

Example 12

Figure 21:
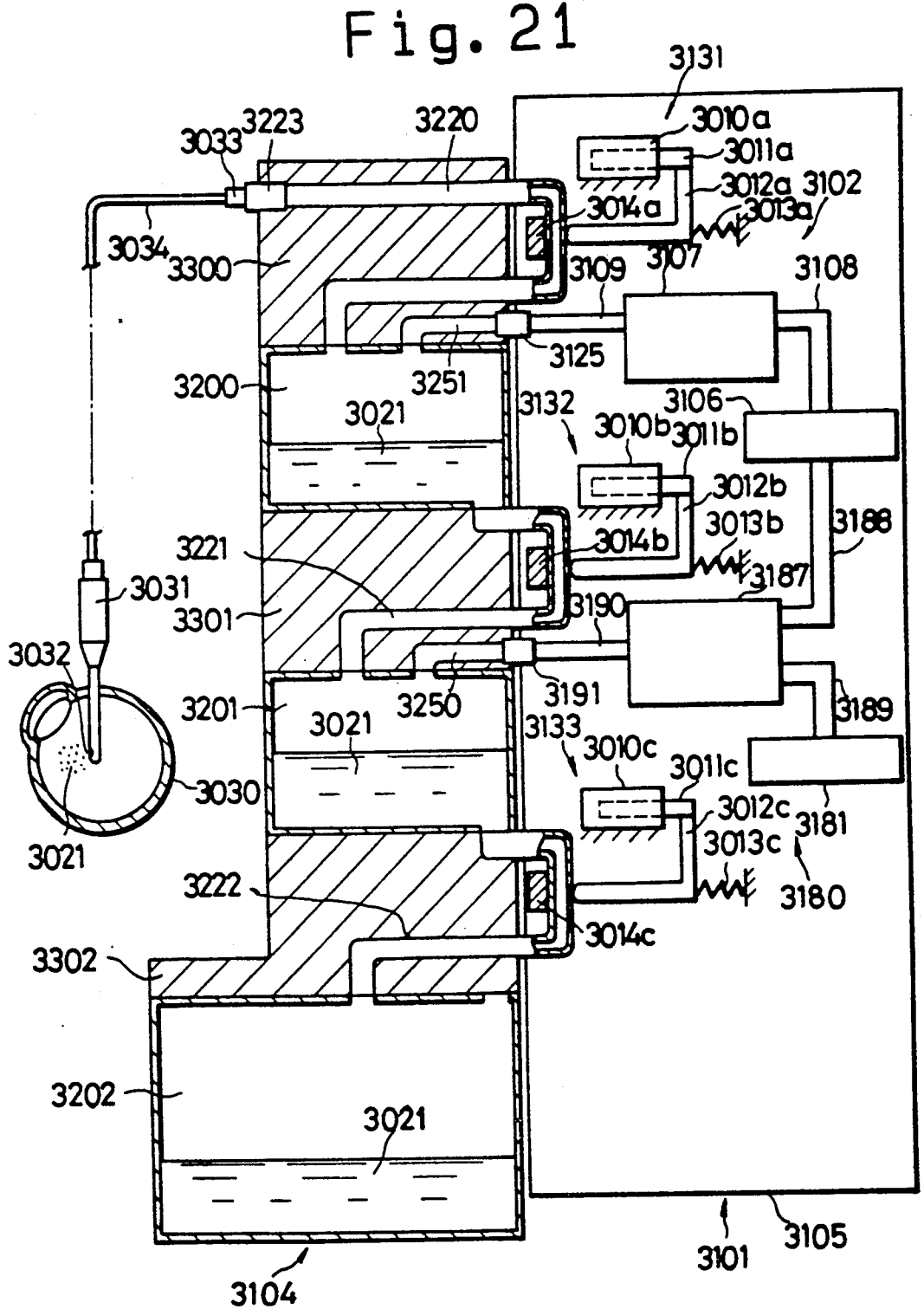
FIG. 21 is a view showing Example 12 according to the present invention.

FIG. 21 shows an aspirator 3101. The aspirator 3101 includes a vacuum controlling unit 3102, a main body 3105, materials-passage opening/closing units 3131-3133, a pressure controlling unit 3180, and an aspirating cassette 3104. A vacuum pump 3106 of the vacuum controlling unit 3102, a pressure adjusting unit 3107, and the materials-passage opening/closing units 3131-3133 are operated in substantially the same manner as in Example 1. The vacuum pump 3106 and the pressure adjusting unit 3107 are connected to a passage 108.

The pressure controlling unit 3180 includes a compression pump 3181, a pressure adjusting unit 3187, and passages 3188, 3189, and 3190.

The passage 3188 is interconnected between the vacuum pump 3106 and the pressure adjusting unit 3187 and the passage 3189 is interconnected between the compression pump 3181 and the pressure adjusting unit 3187. The passage 3190 is connected at its one end to the pressure adjusting unit 3187 and its other end is an open end. Although the pressure controlling unit 3180 works in substantially the same manner as the vacuum controlling unit 3102, air with reduced pressure flowing from the vacuum pump 3106 to the passage 3190 within the pressure adjusting unit 3102 is replaced by compressive air of the compression pump 3181 and flows in place thereof as a certain signal comes. As the signal is released, the pressure adjusting unit works as the vacuum controlling unit 3102 and reduced air flows.

As a structuring element of each of the materials-passage opening/closing units 3131-3133 has substantially the same structure as the materials-passage opening/closing unit 3003 of Example 11, they are provided with the same reference numerals with suffixes a, b, and c.

The aspirating cassette 3104 is provided with bottles 3200 and 3201, each having substantially the same capacity, and with a bottle 3202 having a capacity larger than each of the previous ones.

A flexible tube 3221 connects the bottle 3200 to the bottle 3201. A flexible tube 3222 connects the bottle 3201 to the bottle 3202. A controlling portion 3191 of the passage 3190 is connected to a tube 3250. The controlling adjusting unit 3107 is connected to the vacuum pump through the passage 3108. A controlling portion 3125 of the passage 3109 is connected to a tube 3251.

Each of the bottles 3200-3202 is provided with each of bottle heads 3300-3302, respectively.

The flexible tube 3220 of the bottle head 3300 is disposed to pass between an L-shaped arm 3012a and a stopper 3014a of the materials-passage opening/closing unit 3131. The flexible tube 3221 of the bottle head 3301 is disposed so as to pass between an L-shaped arm 3012b and a stopper 3014b of the materials-passage opening/closing unit 3132.

A flexible tube 3222 of the bottle head 3302 is disposed so as to pass between an L-shaped arm 3012c and a stopper 3014c of the materials-passage opening/closing unit 3133.

An aspirating mouth portion 3223 of the flexible tube 3220 is connected to a cutter 3031 through a connector 3033 and a tube 3034.

Operation of Aspiration

When the aspirating cassette 3104 is mounted to the main body 3105 of the aspirator, the flexible tube 3220 is located between the L-shaped arm 3012a and the stopper 3014a, the flexible tube 3221 between the L-shaped arm 3012b and the stopper 3014b, and the flexible tube 3222 between the L-shaped arm 3012c and the stopper 3014c, as well as the connecting portion 3125 is connected to the open end of the passage 3109 and the connecting portion 3191 is connected to the open end of the passage 3190.

The connector 3033 of the cutter 3031 is mounted to the aspirating mouth portion 3223 of the aspirating cassette 3104. When an electric source of the aspirator is turned on, the vacuum pump 3106 and the compression pump 3181 are turned on and the solenoids 3010a to 3010c of the respective materials-passage opening/closing units 3131 to 3133 are turned on, thereby squeezing the respective flexible tubes 3220 to 3222.

When aspiration starts as the foot switch or the like (not shown) is turned on, air with its pressure reduced by means of the vacuum controlling unit 3102 is supplied through the passage 3109 to the bottle 3200 and the bottle 3200 is reduced to vacuum. At the same time, the bottle 3201 is reduced to vacuum so as to cause a vacuum pressure lower than the vacuum pressure within the bottle 3200 by means of the pressure controlling unit 3180. Furthermore, at the same time, the solenoid 3010a is turned off so as to allow the flexible tube 3220 to pass therethrough.

The removed materials 3021 within the eyeball 3030 are removed through the aspirating mouth 3032 of the cutter 3031 and conveyed to and accommodated in the bottle 3200 through the tube 3034, the connector 3033, the aspirating mouth portion 3223, and the flexible tube 3220.

When a signal comes at this time from a detector (not shown) mounted to the bottle 3200 such that the bottle 3200 is filled with the removed materials 3021, the solenoid 3010b is turned off to allow them to pass through the flexible tube 3221 and to convey the removed materials 3021 within the bottle 3200 to the bottle 3201.

When a signal comes from a detector (not shown) mounted to the bottle 3201 when the bottle 3201 is filled with the removed materials 3021, the solenoid 3010b is turned on to squeeze the flexible tube 3221 and, at the same time, the solenoid 3010c is turned off so as bring the flexible tube 3222 into a state in which the removed materials pass therethrough. At the same time, as compressed air is brought into a state that it can flow from the pressure controlling unit 3180, the removed materials 3021 within the bottle 3201 are conveyed to the bottle 3202 by means of a force of compressed air. At this time, as the bottle 3201 becomes empty, the solenoid 3010c is turned on to squeeze the flexible tube 3222. At the same time, the pressure controlling unit 3180 reduces the bottle 3201 to vacuum at a pressure lower than the vacuum pressure of the vacuum controlling unit 3102.

In order to stop aspiration, the foot switch or the like is turned off to change the pressure of the vacuum controlling unit 3102 into atmospheric pressure, thereby turning the bottle 3201 to atmospheric pressure. The pressure of the pressure controlling unit 3180 is likewise turned to atmospheric pressure. At the same time, the solenoid 3010a is turned on to squeeze the flexible tube 3220, thereby closing passage of the removed materials 3021 and consequently suspending aspiration.

As the bottle 3202 becomes full, the solenoids 3010a and 3010c are forcibly turned on to squeeze the respective flexible tubes 3220 and 3222 regardless of the ON state of the foot switch or the like. At the same time, pressures of the bottles 3200 and 3201 are turned into atmospheric pressure by means of the vacuum controlling unit 3102 and the pressure controlling unit 3180, thereby forcibly suspending aspiration.

The present invention may encompass the following modes within the scope thereof.

The materials-passage opening/closing unit may be one in which an air cylinder, a motor or the like is used, in addition to one in which a solenoid is employed.

On top of the type in which the flexible tube is squeezed to close passage of the removed materials, there may be used a type in which the flexible tube is bent, blocking passage thereof.

When the flexible tube is squeezed blocking passage of the removed materials, it may be squeezed by pressing the arm from multiple directions on top of the pressing from one direction.

When the aspirating cassette is mounted, the flexible tube is located at a position between the arm and the stopper. As the aspirating cassette is mounted, the flexible tube may be located at the materials-passage opening/closing unit by picking the flexible tube by means of a robot hand or other means.

The aspirating cassette is not restricted to one or three bottles and it may be another number of multiple bottles.

The positions of the arm and the stopper for squeezing the flexible tube are not restricted to those as shown in FIGS. 19 and 21, and they may be disposed to squeeze the flexible tube in a direction perpendicular to each other.

In place of the flexible tubes 3020, 3220, 3221, and 3222, there may be used one in which only a portion of the tube may be formed by a flexible material and the rest may be formed by a non-flexible material. The flexible portion may be located between the stopper 14 and the L-shaped arm 3012.

As a conveyance of the removed materials within a flexible passage in the aspirating cassette can be carried out or suspended merely by means of the materials-passage opening/closing unit in the aspirator, regardless of aspirating vessels. Thus, as no force is applied to the aspirating vessels, there is no possibility that the vessels are caused to be inclined or detached from the aspirator portion so that the surgery can be carried out with safety.

INDUSTRIAL APPLICABILITY

The present invention is particularly useful for aspirating materials to be removed from the eyeball and ensures a safe surgery.

We claim:

1. An adjustable pressure aspirator comprising:
   aspirating means for removing material by aspiration;
   a receiving vessel connected to said aspirating means, said receiving vessel having an interior for collecting the material removed by aspiration;
   vacuum means for producing a vacuum pressure within said receiving vessel;
   pressure detecting means for detecting said vacuum pressure within said receiving vessel;
   a vent for connecting the interior of said receiving vessel with atmosphere external to said vessel, said vent having an opening of variable size; and
   pressure control means for controlling the vacuum pressure within the interior of said receiving vessel to maintain a constant pressure by adjusting the size of said opening, responsive to said detected vacuum pressure.

2. An adjustable pressure aspirator in accordance with claim 1 wherein said vent has elastic wall means for defining said opening and wherein said pressure control means adjusts said sides of said opening by pressing against said elastic wall means.

3. An aspirator in accordance with claim 1 further comprising a manual switch for setting said constant pressure at a desired level.

4. An aspirator in accordance with claim 3 wherein said manual switch is a foot switch.

5. An adjustable pressure aspirator comprising:
   aspirating means for removing material by aspiration;
   a first receiving vessel connected to said aspirating means, said first receiving vessel having an interior for collecting the material removed by aspiration;
   a second receiving vessel having an interior for collecting the material removed by aspiration, said interior of said second receiving vessel having substantially the same capacity as said interior of said first receiving vessel;
   a first passage for transferring the collected material from said first receiving vessel to said second receiving vessel;
   a valve mounted in said first passage for opening or closing said first passage;
   vacuum means, interconnected between said first and second receiving vessels, for establishing a vacuum within said first and second receiving vessels;
   pressure detecting means for detecting pressure within said first receiving vessel;
   a vent for connecting the interior of said first receiving vessel with atmosphere external to said first receiving vessel, said vent having an opening of variable size; and
   pressure control means for controlling the vacuum within said first receiving vessel at a constant pressure by adjusting the size of said opening, responsive to said detected pressure.

6. An adjustable pressure aspirator in accordance with claim 5 wherein said vent has elastic wall means for defining said opening and wherein said pressure control means adjusts said sides of said opening by pressing against said elastic wall means.

7. An adjustable pressure aspirator comprising:
   aspirating means for removing material by aspiration;
   a first receiving vessel connected to said aspirating means, said first receiving vessel having an interior for collecting the material removed by aspiration;
   a second receiving vessel having an interior for collecting material removed by aspiration, said interior of said second receiving vessel having a capacity larger than said interior of said first receiving vessel;
   a first elastic conduit for passage of the collected material from said first receiving vessel to said second receiving vessel;
   constricting means for repeatedly constricting said first elastic conduit to convey the collected material through said first elastic conduit;
   vacuum means for establishing a vacuum within said interior of said first receiving vessel;
   pressure detecting means for detecting pressure within said interior of said first receiving vessel;
   a vent for connecting the interior of said first receiving vessel with atmosphere external to said first receiving vessel, said vent having an opening of variable size; and
   pressure control means for controlling the vacuum within said first receiving vessel at a constant pressure by adjusting the size of said opening, responsive to said detected pressure.

8. An adjustable pressure aspirator in accordance with claim 7 wherein said vent has elastic wall means for defining said opening and wherein said pressure control means adjusts said sides of said opening by pressing against said elastic wall means.

9. An aspirator for removing material by vacuum comprising:
   a first receiving vessel for collecting the material removed by vacuum;
   a second receiving vessel for collecting the material removed by vacuum;
   a third receiving vessel for collecting the material removed by vacuum, said third receiving vessel having a capacity larger than said first receiving vessel and larger than said second receiving vessel;
   an aspirating instrument for applying the vacuum to the material to be removed;
   a first passage for conveyance of the removed material from said aspirating instrument to said first receiving vessel;
   first vacuum means for producing a vacuum within said first receiving vessel;
   second vacuum means for producing a vacuum within said second receiving vessel;
   a second passage, separate from said first passage, for conveyance of the collected material from said first collecting vessel to said second collecting vessel;
   a first valve provided within said second passage for opening or closing said second passage;
   a third passage, separate from said second passage, for conveyance of the collected material from said second receiving vessel to said third receiving vessel; and
   a second valve provided within said third passage for opening or closing said third passage;
   whereby a pressure within said second receiving vessel not higher than the pressure within said first receiving vessel will cause conveyance of the collected material from said first receiving vessel to said second receiving vessel and wherein a pressure within said second receiving vessel higher than the pressure within said third receiving vessel will cause conveyance of the collected material within said second receiving vessel to said third receiving vessel, through said third passage.

10. An aspirator in accordance with claim 9 additionally comprising a first level detector for detecting the level of material collected within said first receiving vessel;

a second level detector for detecting the level of material collected within said second receiving vessel;

wherein said first valve opens responsive to detection of a predetermined level within said first receiving vessel to allow the collected material to transfer to said second receiving vessel through said second passage;

wherein said first valve closes responsive to the detected level within said first receiving vessel falling below said predetermined level.

11. An aspirator in accordance with claim 9 further comprising:

first pressure detecting means for detecting pressure within said first receiving vessel; and wherein said first vacuum means is responsive to said pressure detected by said first pressure detecting means to maintain a substantially constant vacuum within said first receiving vessel.

12. An aspirator in accordance with claim 11 further comprising second pressure detection means for detecting pressure within said second receiving vessel; and wherein said second vacuum means adjusts the degree of vacuum within said second receiving vessel responsive to the pressure detected by said second pressure detection means.

13. An aspirator for removing material by vacuum, said aspirator comprising:

a plurality of receiving vessels for collecting the material removed by vacuum;

vacuum means for establishing a vacuum within each said receiving vessel;

a housing for each said vacuum means, said receiving vessel being detachably mounted to said housing;

an aspirating tool for applying said vacuum to the material to be removed;

a plurality of conduits, each of said conduits having, at least a portion which is elastic, for conveying the removed material from said aspirating tool to said receiving vessel; and constricting means, mounted within each of said housings, for limiting flow through each of said conduits by deformation of said elastic portion.

14. An aspirator in accordance with claim 13 wherein said constricting means includes a manual switch, a solenoid valve operative in response to said manual switch and a plunger in contact with said flexible portion and movable by said solenoid valve.

15. An aspirator in accordance with claim 14 further comprising a level detector for detecting a predetermined level of collected material in each said receiving vessel and for generating a full signal responsive to detection of each said predetermined signal, said constricting means being responsive to said full signal by closing each said respective conduit.

* * * * *

UNITED STATES PATENT AND TRADEMARK OFFICE
CERTIFICATE OF CORRECTION

PATENT NO. : 5,195,961

DATED : March 23, 1993

INVENTOR(S) : TAKAHASHI et al

It is certified that error appears in the above-identified patent and that said Letters Patent is hereby corrected as shown below:

Col. 1, line 22, "o" should read --or--;

line 46, "each" should read --reach--.

Col. 5, line 44, "n" should read --no--.

Col. 13, line 23, "o" should read --or--.

Col. 15, line 29, "ar" should read --are--.

Col. 17, line 20, "a" should read --as--.

Col. 19, line 52, "o" should read --on--.

Signed and Sealed this

Fifteenth Day of February, 1994

*Attest:*

BRUCE LEHMAN

*Attesting Officer*      *Commissioner of Patents and Trademarks*